US011235046B2

(12) United States Patent
Brett et al.

(10) Patent No.: US 11,235,046 B2
(45) Date of Patent: Feb. 1, 2022

(54) IMMUNOGENIC CONJUGATES AND METHODS OF USE THEREOF

(71) Applicant: BOARD OF REGENTS OF THE NEVADA SYSTEM OF HIGHER EDUCATION, ON BEHALF OF THE UNIVERSITY OF NEVADA, Reno, NV (US)

(72) Inventors: Paul J. Brett, Reno, NV (US); Mary N. Burtnick, Reno, NV (US)

(73) Assignee: Nevada Research & Innovation Corporation, Reno, NV (US)

( * ) Notice: Subject to any disclaimer, the term of this patent is extended or adjusted under 35 U.S.C. 154(b) by 0 days.

(21) Appl. No.: 16/760,418

(22) PCT Filed: Nov. 2, 2018

(86) PCT No.: PCT/US2018/059043
§ 371 (c)(1),
(2) Date: Apr. 29, 2020

(87) PCT Pub. No.: WO2019/090138
PCT Pub. Date: May 9, 2019

(65) Prior Publication Data

US 2020/0338179 A1 Oct. 29, 2020

Related U.S. Application Data

(60) Provisional application No. 62/581,700, filed on Nov. 4, 2017.

(51) Int. Cl.

| | |
|---|---|
| *A61K 39/02* | (2006.01) |
| *A61K 47/64* | (2017.01) |
| *A61P 31/04* | (2006.01) |
| *A61K 39/00* | (2006.01) |

(52) U.S. Cl.
CPC ............ *A61K 39/02* (2013.01); *A61K 47/646* (2017.08); *A61K 47/6415* (2017.08); *A61P 31/04* (2018.01); *A61K 2039/6037* (2013.01)

(58) Field of Classification Search
None
See application file for complete search history.

(56) References Cited

U.S. PATENT DOCUMENTS

| | | | |
|---|---|---|---|
| 8,778,356 | B2 | 7/2014 | Prior et al. |
| 2015/0273043 | A1 | 10/2015 | Wacker et al. |

OTHER PUBLICATIONS

International Search Report and Written Opinion for PCT/US2018/059043 dated May 9, 2019; 11 pages.
Burtnick, Mary N., et al., Development of Subunit Vaccines That Provide High-Level Protection and Sterilizing Immunity against Acute Inhalational Melioidosis, American Society for Microbiology Infection and Immunity vol. 86, No. 1, Jan. 2018, 15 pages.
Lim, Yan Ting, et al., Extended Loop Region of Hcp1 is Critical for the Assembly and Function of Type VI Secretion System in Burkholderia pseudomallei, Scientific Reports, Feb. 4, 2015, 10 pages.
Suttisunhakul, Vichaya, et al., Development of Rapid Enzyme-Linked Immunosorbent Assays for Detection of Antibodies to Burkholderia pseudomallei, American Society for Microbiology Infection and Immunity vol. 54, No. 5, May 2016, 10 pages.

*Primary Examiner* — Padmavathi Baskar
(74) *Attorney, Agent, or Firm* — Schwabe, Williamson & Wyatt PC

(57) ABSTRACT

Disclosed are capsular polysaccharide (CPS)-protein immunogenic conjugates useful for providing protection against any condition or disease associated with *Burkholderia pseudomallei* or *Burkholderia mallei*, such as melioidosis or glanders, respectively. For example, a disclosed CPS-protein immunogenic conjugate includes purified 6-deoxyheptan capsular polysaccharide (CPS) from *B. pseudomallei* chemically activated and covalently linked to recombinant CRM 197 diphtheria toxin mutant (CRM197) to produce CPS-CRM197. Methods of inducing an immune response are disclosed. The methods include the use of a CPS-protein immunogenic conjugate, alone or in conjunction with other agents, such as Hcp1 and TssM, to prevent infection with *B. pseudomallei* or *B. mallei*. Also disclosed are methods for treating a subject having melioidosis or glanders.

11 Claims, 11 Drawing Sheets

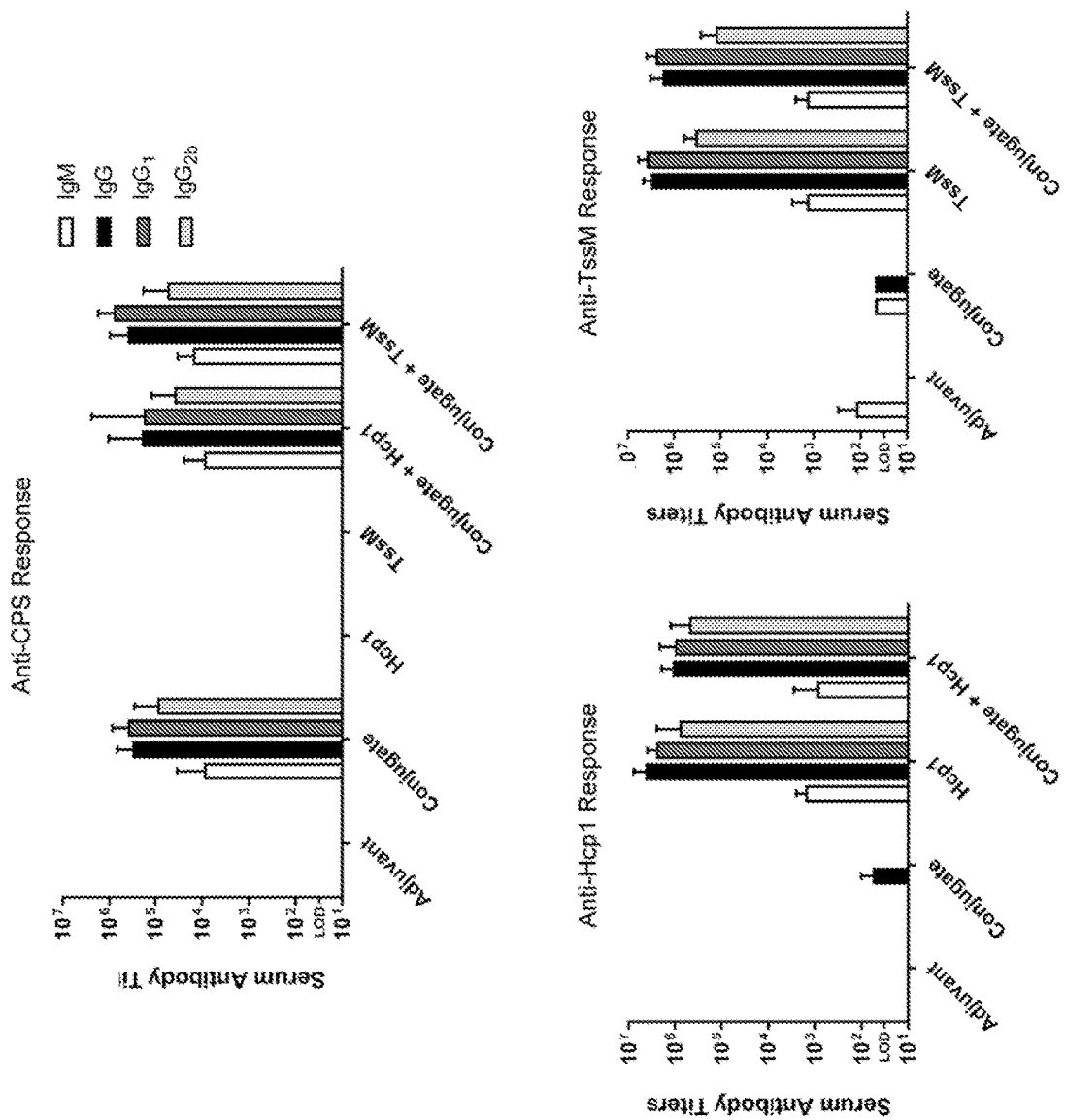

FIG. 5A
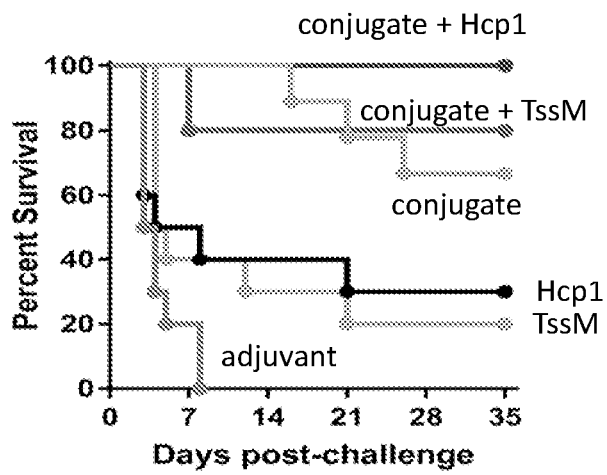
FIG. 5B
FIG. 5C
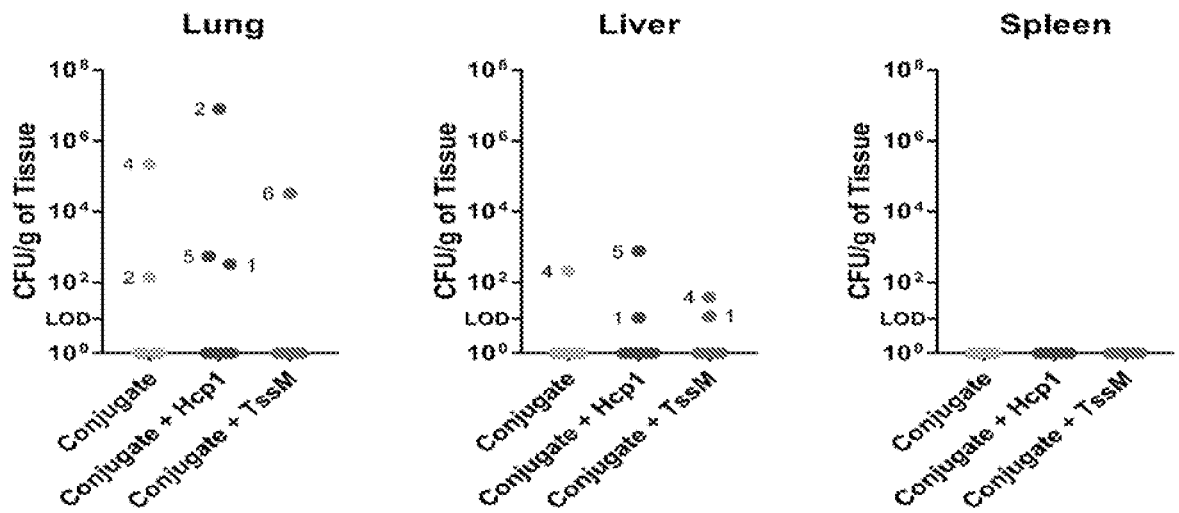

IMMUNOGENIC CONJUGATES AND METHODS OF USE THEREOF

CROSS REFERENCE TO RELATED APPLICATION

This application is the US National Stage Application under 35 USC 371 of International Application PCT/US2018/059043, filed Nov. 2, 2018, which claims the benefit of U.S. Provisional Application No. 62/581,700, filed Nov. 4, 2017, which is hereby incorporated by reference in its entirety.

ACKNOWLEDGMENT OF GOVERNMENT SUPPORT

This invention was made with government support under contract HDTRA1-14-C-0023 awarded by the Defense Threat Reduction Agency. The government has certain rights in the invention.

FIELD

This disclosure relates to immunogenic conjugates and in particular, capsular polysaccharide-protein immunogenic conjugates for providing protection against any condition or disease associated with *Burkholderia pseudomallei* or *Burkholderia mallei*, such as melioidosis or glanders, respectively.

BACKGROUND

Melioidosis is an emerging infectious disease that is being increasingly recognized in tropical regions around the world. While it is known to be endemic in at least 48 different countries in Southeast Asia, South Asia, the Middle East, Africa, Central America and South America, current models predict that the disease is probably endemic in 34 additional countries where it has yet to be reported (1). Under-recognition of melioidosis is due, in part, to the fact that most cases occur in resource-poor countries with large rural populations and limited microbiological laboratory capabilities (2). Since the clinical presentations of melioidosis are diverse, ranging from skin abscesses to acute pneumonias and septicemias, diagnosis can be difficult. In 2015, the estimated total global burden of human melioidosis was ~165,000 cases with ~89,000 deaths which is equivalent to that of measles and exceeds the levels of leptospirosis and dengue infection, underscoring the potential impact of the disease worldwide (1).

*Burkholderia pseudomallei*, the etiologic agent of melioidosis, is a facultative intracellular Gram-negative bacterium that can be isolated from environmental niches such as rice paddies, still or stagnant waters, and moist soils in endemic areas. Humans can acquire *B. pseudomallei* infections through percutaneous inoculation via skin abrasions during occupational or recreational exposure, inhalation of bacteria in aerosolized dust or water, or ingestion of contaminated water (3, 4). Most natural infections occur in individuals with one or more risk factors such as diabetes, alcoholism, chronic pulmonary disease, chronic renal disease or thalassemia (5-8). At present, the association between route of infection and the clinical manifestations of melioidosis is not clearly defined. Recent studies, however, have demonstrated a link between inhalation of aerosolized *B. pseudomallei* during severe weather events and pneumonia (9-12). Notably, over half of all melioidosis cases present as pneumonias which can range from mild to severe disease (13).

In addition to being an important public health concern, *B. pseudomallei* is also considered a potential biological weapon and is currently categorized as a Tier 1 select agent by U.S. Centers for Disease Control and Prevention (14, 15). In the event of an intentional release, it is believed that the most likely mode of dissemination would be via infectious aerosols leading to respiratory disease. Since *B. pseudomallei* is intrinsically resistant to many conventionally used antibiotics, treatment of melioidosis can be complicated. For culture confirmed cases, the currently recommended antibiotic regimens are lengthy and typically involve a minimum of two weeks of intravenous therapy followed by up to six months of oral therapy (13). The ability of *B. pseudomallei* to persist inside of host cells makes eradication of infections difficult and even with appropriate chemotherapeutic intervention, relapse is possible (13). Furthermore, re-infection with a different *B. pseudomallei* strain can occur following successful treatment. At present, there are no human vaccines available for immunization against melioidosis. Because of these challenges, the development of medical countermeasures to combat melioidosis has become a priority in recent years (16).

SUMMARY

An ideal melioidosis vaccine would be one that provides long-term protection against the most severe forms of the disease, namely acute pneumonia and septicemia, and broad-spectrum protection against multiple *B. pseudomallei* strains. Several different live-attenuated vaccine strains as well as *B. pseudomallei*-derived outer membrane vesicles (OMVs) have been evaluated in pre-clinical studies and shown to confer significant protection in animal models of melioidosis (17-20). There are, however, important safety concerns associated with these types of vaccines. Numerous studies have also shown that *B. pseudomallei* expresses a variety of structurally conserved protective antigens. These include cell-surface polysaccharides (e.g. 6-deoxyheptan capsular polysaccharide (CPS) and lipopolysaccharide), cell-associated proteins (e.g. LolC, OmpA, OmpW and FliC) and secreted proteins (e.g. BopA, BimA, FlgL and MprA) (16, 21-29). Although these subunit vaccine candidates offer safety advantages over the use of live-attenuated strains and OMVs, none have been able to provide complete protection and sterilizing immunity when tested alone (16).

Since CPS is structurally conserved and expressed by all known virulent isolates of *B. pseudomallei*, it is an attractive antigen for vaccine development (26, 30). Supporting this, CPS-specific monoclonal antibodies (mAbs) have been used to passively immunize mice against lethal challenges of *B. pseudomallei* (21, 28). Recently, immunization of BALB/c mice with a CPS-cBSA glycoconjugate resulted in high CPS-specific IgG titers conferring significant protection against a *B. pseudomallei* challenge (26). In addition, when immunized with a combination of CPS-cBSA and recombinant LolC, compared to each component alone, mice exhibited higher survival rates when challenged with a lethal intraperitoneal dose of *B. pseudomallei* (26). Based upon these observations, a subunit vaccine formulation that stimulates both protective humoral and cellular immune responses is disclosed herein to provide full protection against *B. pseudomallei* infections.

In the present disclosure, a combination of molecular genetic, biochemical and immunological approaches were used to evaluate the immunogenicity and protective capacity of a CPS-based glycoconjugate combined with either a hemolysin co-regulated protein (Hcp1) or a deubiquitinase (TssM). Herein, it is demonstrated for the first time, that subunit vaccine formulations containing these antigens provide C57BL/6 mice with high level protection and sterilizing immunity against an acute inhalational challenge of *B. pseudomallei*.

Based upon these findings, disclosed are capsular polysaccharide-protein conjugates, vaccines and methods of use thereof, such as for providing protection against any condition or disease associated with *Burkholderia*, such as *Burkholderia pseudomallei* or *Burkholderia mallei*, including melioidosis (acute and/or chronic) or glanders. Methods of inducing an immune response to *Burkholderia pseudomallei* or *Burkholderia mallei* are disclosed. Methods for treating a subject with melioidosis or at risk of acquiring it are also disclosed which include administering effective concentrations of a disclosed conjugate to protect the subject from melioidosis or inhibit one or more sign or symptoms associated with melioidosis. In some examples, these methods are used to prevent, reduce and/or inhibit infection by inhalation of *Burkholderia pseudomallei* produced during a bioterrorism event. Methods are also disclosed for treating a subject with glanders or at risk of acquiring it, which include administering effective concentrations of a disclosed conjugate to protect the subject from glanders or inhibit one or more sign or symptoms associated with glanders.

The foregoing and other features will become more apparent from the following detailed description of several embodiments, which proceeds with reference to the accompanying figures.

BRIEF DESCRIPTION OF THE FIGURES

(FIG. 1A) Basic conjugation strategy used to couple purified *B. pseudomallei* CPS to recombinant CRM197. (FIG. 1B) SDS-PAGE and Coomassie Blue staining were used to assess the covalent linkage of CPS to CRM197 in phosphate buffered saline (PBS) or borate buffer (BB). Samples were drawn from the reaction mixtures on days 0, 1, 3, 7 and 10. Day 0 represents unconjugated controls. All lanes were loaded with equal amounts of protein to facilitate direct comparisons. The positions of the protein molecular weight standards (kDa) are indicated on the left.

FIGS. 2A-2C. Characterization of antibody titers raised against CPS-CRM197, Hcp1 and TssM. C57BL/6 mice (n=6 per group) were immunized on days 0, 21 and 35 with adjuvant only (Alhydrogel/CpG), conjugate only, Hcp1 only, TssM only, conjugate plus Hcp1 and conjugate plus TssM. Immune serum samples were collected for testing on day 42. ELISAs were used to quantitate serum IgM, IgG, IgG1 and IgG2b titers against (FIG. 2A) CPS, (FIG. 2B) Hcp1 and (FIG. 2C) TssM. Bars represent geometric means with 95% CI. Conjugate=CPS-CRM197; LOD=limit of detection.

FIGS. 5A-5C. Protective capacity of the subunit vaccine formulations tested in this study. C57BL/6 mice (n=9-10 mice per group) were immunized on days 0, 21 and 35 with adjuvant only (Alhydrogel/CpG), conjugate only, Hcp1 only, TssM only, conjugate plus Hcp1 and conjugate plus TssM. Five weeks after the final boost, mice were challenged via an inhalational route with ~10 $LD_{50}$ of *B. pseudomallei* K96243. (FIG. 5A) Mice were monitored for 35 days post-challenge and their survival plotted. (FIG. 5B) Significance for survival was determined using a log-rank (Mantel-Cox) test. (FIG. 5C) At the end of the study, survivors were culled (n=10 for conjugate plus Hcp1; n=8 for conjugate plus TssM and n=6 for conjugate only), organs were removed and bacterial loads determined. Individual mice are designated by numbers next to the respective dots. Conjugate=CPS-CRM197.

K96243 as described herein (see Examples). Mice were monitored for survival over 35 days and the $LD_{50}$ calculated.

Figure 10:
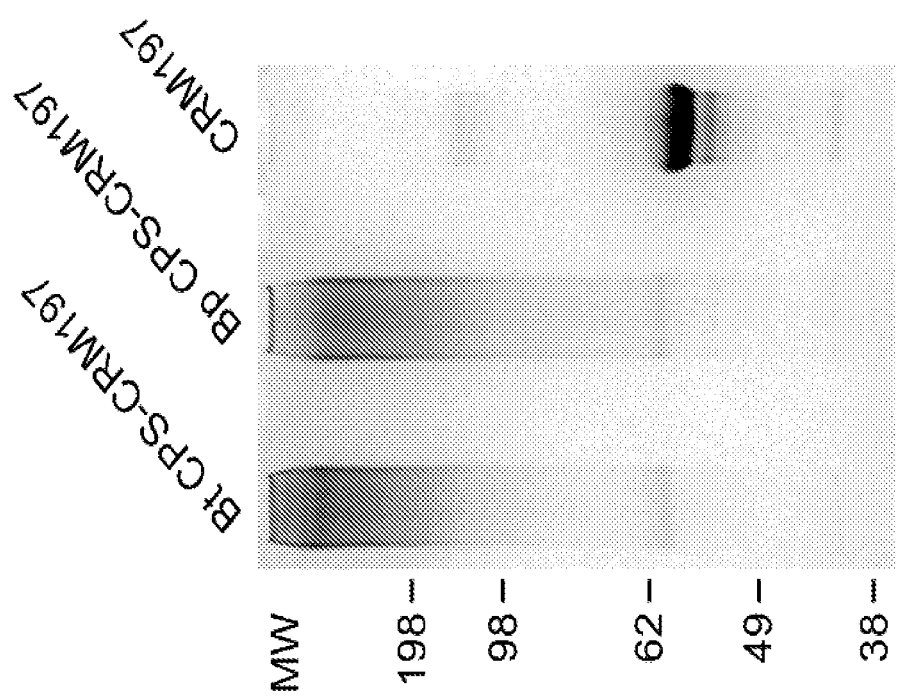

FIG. 10. SDS-PAGE analysis of CPS-CRM197 glycoconjugates. Bt CPS-CRM197 (7.5 μg), Bp CPS-CRM197 (7.5 μg) and CRM917 (3 μg; control) were separated on a 4-12% Bis-Tris Bolt gel and visualized with SimplyBlue Safe Stain (see Examples). The protein molecular standards (kDa) are indicated on the left. Bt CPS-CRM197 contains ~60% (w/w) CPS while Bp CPS-CRM197 contains ~54% (w/w) CPS.

FIG. 11. Western immunoblot analysis of CPS-CRM197 glycoconjugates. Bt CPS-CRM197 (2.5 μg), Bp CPS-CRM197 (2.5 μg) and CRM917 (1 μg; control) were separated on a 4-12% Bis-Tris Bolt gel and electrophoretically transferred to a nitrocellulose membrane. CPS was detected using the *Burkholderia pseudomallei* CPS-specific mAb, 4C4. The positions of the protein molecular standards (kDa) are indicated on the left. Bt CPS-CRM197 contains ~60% (w/w) CPS while Bp CPS-CRM197 contains ~54% (w/w) CPS.

DETAILED DESCRIPTION OF SEVERAL EMBODIMENTS

I. Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a "biological adjuvant"), such as costimulatory molecules.

Administration: The introduction of a composition into a subject by a chosen route. Administration can be systemic or local. For example, if the chosen route is intravenous, the composition is administered by introducing the composition into a vein of the subject, and if the chosen route is intramuscular, the compositing is administered by introducing the composition into a muscle.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Antibody: Immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', $F(ab')_2$ and F(v), as well as chimeric antibody molecules.

*Burkholderia*: A genus of Proteobacteria whose pathogenic members include *Burkholderia pseudomallei*, causative agent of melioidosis; and *Burkholderia mallei*, responsible for glanders, a disease that occurs mostly in horses and related animals; and *Burkholderia cepacia*, a pathogen of pulmonary infections in people with cystic fibrosis. *Burkholderia thailandensis* is a nonfermenting motile, Gram-negative bacillus that occurs naturally in soil. It is closely related to *Burkholderia pseudomallei*, but unlike *B. pseudomallei*, it only rarely causes disease in humans or animals. The lethal inoculum is approximately 1000 times higher than for *B. pseudomallei*. It is usually distinguished from *B. pseudomallei* by its ability to assimilate arabinose. Other differences between these species include lipopolysaccharide composition, colony morphology, and differences in metabolism.

The *Burkholderia* (previously part of *Pseudomonas*) genus name refers to a group of virtually ubiquitous Gram-negative, obligately aerobic, rod-shaped bacteria that are motile by means of single or multiple polar flagella, with the exception of *Burkholderia mallei* which is nonmotile. Members belonging to the genus do not produce sheaths or prosthecae and are able to utilize poly-beta-hydroxybutyrate (PHB) for growth. The genus includes both animal and plant pathogens.

*Burkholderia*-associated molecule: A molecule associated with a pathogenic or non-pathogenic member of this genus of Proteobacteria, such as Hcp1 or TssM.

Capsular polysaccharide (CPS): A bacterial extracellular polysaccharide that is intimately associated with the cell surface. An example is 6-deoxyheptan capsular polysaccharide (CPS) from *B. pseudomallei.*

Carrier Protein: A protein that transports specific substance through intracellular compartments, into the extracellular fluid, or across the cell membrane.

Chemical derivative: A modified oligo- or poly-saccharide having one or more residues chemically derivatized by reaction of a functional side group. For example, one or more hydroxyl groups of the oligo- or poly-saccharide may be reduced, oxidized, esterified, or etherified; or one or more acetamido groups may be hydrolyzed or replaced with other carboxamido or ureido groups, and suitably disposed pairs of hydroxyl groups may be converted into cyclic phosphate diesters. Such transformations are well-known and within the abilities of those skilled in the art of carbohydrate chemistry. Additional residues may also be added for the purpose of providing a "linker" by which the modified oligo- or poly-saccharide of this invention can be conveniently affixed to a label or solid matrix or carrier. Suitable residues for providing linkers may contain amino, carboxyl, or sulfhydryl groups, for example. Labels, solid matrices and carriers that can be used with the oligo- or poly-saccharide of this disclosure are described herein.

Contacting: Placement in direct physical association; includes both in solid and liquid form. Contacting can occur in vitro with isolated cells or in vivo by administering the agent to a subject.

Deubiquitinase (TssM): A potent deubitiquitinase involved in modulating host immune responses and is secreted by *B. pseudomallei* in a type II secretion system dependent manner. TssM is a *Burkholderia*-associated molecule.

Effective Amount: An amount of agent that is sufficient to generate a desired response, such as reducing or inhibiting one or more signs or symptoms associated with a condition or disease. When administered to a subject, a dosage will generally be used that will achieve target concentrations. In some examples, an "effective amount" is one that treats one or more symptoms and/or underlying causes of any of a disorder or disease. In some examples, an "effective amount" is a "therapeutically effective amount" in which the agent alone with an additional therapeutic agent(s) induces the desired response. Ideally, a therapeutically effective amount of an agent is an amount sufficient to reduce, inhibit, and/or treat the disorder in a subject without causing a substantial cytotoxic effect in the subject. The effective amount of a composition useful for reducing, inhibiting, and/or treating a disorder in a subject will be dependent on the subject being treated, the severity of the disorder, and the manner of administration of the therapeutic composition. Effective amounts a therapeutic agent can be determined in many different ways. Effective amounts also can be determined through various in vitro, in vivo or in situ assays. An effective amount is one which prevents or inhibits one or more signs or symptoms or laboratory findings associated with melioidosis or glanders.

Hemolysin co-regulated protein (Hcp1): Hcp1 is a major structural component of the virulence-associated *B. pseudomallei* type VI secretion system and is expressed in high levels upon activation of this system. As used herein Hcp1 is a *Burkholderia*-associated molecule.

Inhibiting or treating a condition or disease: A phrase used to refer to inhibiting the development of a specific condition or disease, such as any condition or disease associated with *Burkholderia pseudomallei* or *Burkholderia mallei*. In several examples, inhibiting a condition or disease refers to lessening symptoms of melioidosis or glanders. "Treatment" refers to a therapeutic intervention that ameliorates a sign or symptom of a disease or pathological condition related to the disease, such as melioidosis or glanders.

Melioidosis: An infectious disease caused by a Gram-negative bacterium, *Burkholderia pseudomallei*, found in soil and water. It is of public health importance in endemic areas, particularly in Thailand and northern Australia. It exists in acute and chronic forms. Symptoms may include pain in chest, bones, or joints; cough; skin infections, lung nodules and pneumonia. *B. pseudomallei* was thought to be a member of the *Pseudomonas* genus and was previously known as *Pseudomonas pseudomallei*. It is phylogenetically related closely to *Burkholderia mallei* which causes glanders, an infection primarily of horses, donkeys and mules.

Acute melioidosis normally has an incubation period of less than a month. Patients with latent melioidosis may be symptom free for decades. Chronic melioidosis is usually defined by a duration of symptoms greater than 2 months and occurs in approximately 10% of patients. The clinical presentation of chronic melioidosis is protean and includes such presentations as chronic skin infection, skin ulcers and lung nodules or chronic pneumonia. A patient with active melioidosis may present a fever or other pain or other symptoms such as cough, pleuritic chest pain, bone or joint pain, or intra-abdominal infection (including liver and/or splenic abscesses, or prostatic abscesses).

A current treatment of melioidosis may be divided into two stages, an intravenous high intensity stage and an oral maintenance stage to prevent recurrence. The intravenous intensive phase may include the following. Intravenous ceftazidime for treatment of acute melioidosis. Meropenem, imipenem and cefoperazone-sulbactam (Sulperazone) are also active. Intravenous amoxicillin-clavulanate (co-amoxiclav) may also be used. Intravenous antibiotics are typically given for a minimum of 10 to 14 days, and are continued until the patient's temperature has returned to normal for more than 48 hours: it is not uncommon for patients to require parenteral treatment continuously for more than a month. Additional possible therapeutic agents include cefepime, ertapenem, piperacillin-sulbactam, doripenem and biapenem.

Following the treatment of the acute disease, a maintenance treatment may be provided to the patient such as administration of co-trimoxazole and doxycycline for a period of time (such as 12 to 20 weeks) to reduce the rate of recurrence. Other maintenance treatments may include administration of chloramphenicol and co-amoxiclav.

A "non-melioidosis" or "normal" subject does not have any form of melioidosis.

Oligosaccharide: A carbohydrate containing up to twelve monosaccharide units linked together.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition (1995), describes compositions and formulations suitable for pharmaceutical delivery of the conjugates and compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polysaccharide: A carbohydrate containing more than twelve monosaccharide subunits linked together.

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease.

Symptoms for melioidosis may include pain in chest, bones, or joints; cough; skin infections, lung nodules and pneumonia. The clinical presentation of chronic melioidosis is protean and includes such presentations as chronic skin infection, skin ulcers and lung nodules or chronic pneumonia. A patient with active melioidosis may present a fever or other pain or other symptoms such as cough, pleuritic chest pain, bone or joint pain, or intra-abdominal infection (including liver and/or splenic abscesses, or prostatic abscesses).

Subject: Living multi-cellular vertebrate organisms, a category that includes human and non-human mammals. In an example, a subject is a human.

Substitute ("substituted" or "substitution"): Use of a chemically derivatized residue in place of a non-derivatized residue provided that the resulting modified oligo- or polysaccharide displays the requisite immunological activity.

Under conditions sufficient for: A phrase that is used to describe any environment that permits the desired activity. In one example, includes administering a disclosed composition to a subject sufficient to allow the desired activity.

II. Compositions

Disclosed herein are CPS-protein immunogenic conjugates. In some embodiments, a disclosed CPS-protein immunogenic conjugate comprises purified 6-deoxyheptan capsular polysaccharide (CPS) from *Burkholderia* chemically activated and covalently linked to a carrier protein, such as a recombinant diphtheria toxin mutant to produce CPS-CRM. In some embodiments, the recombinant diphtheria toxin mutant is CRM197. For example, a disclosed CPS-protein immunogenic conjugate comprises purified 6-deoxyheptan capsular polysaccharide (CPS) from *B. pseudomallei, B. thailandensis* or *B. mallei* chemically activated and covalently linked to recombinant CRM197 diphtheria toxin mutant (CRM197) to produce CPS-CRM197.

Also provided are compositions including a disclosed CPS-protein immunogenic conjugates, such as CPS-CRM197 in a physiological vehicle or carrier. In some examples, a composition further includes at least one *Burkholderia*-associated molecules, such as hemolysin co-regulated protein (Hcp1) or deubiquitinase (TssM). For example, a composition comprises CPS-CRM197 and Hcp1 or TssM in a physiological acceptable carrier.

These compositions can be used to generate an immune response. In one embodiment, the composition is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54:110, 1977, and Hunter et al., J. Immunol 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant. Controlled release parenteral formulations can be made as implants, oily injections, or as particulate systems. For a broad overview of protein delivery systems, see Banga, Therapeutic Peptides and Proteins: Formulation, Processing, and Delivery Systems, Technomic Publishing Company, Inc., Lancaster, Pa., 1995. Particulate systems include microspheres, microparticles, microcapsules, nanocapsules, nanospheres, and nanoparticles.

Polymers can be used for ion-controlled release. Various degradable and nondegradable polymeric matrices for use in controlled drug delivery are known in the art (Langer, Accounts Chem. Res. 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., Pharm. Res. 9:425, 1992; and Pec, J. Parent. Sci. Tech. 44(2):58, 1990). Alternatively, hydroxyapatite has been used as a microcarrier for controlled release of proteins (Ijntema et al., Int. J. Pharm. 112:215, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa., 1993). Numerous additional systems for controlled delivery of therapeutic molecules are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2): 122-38; Lotze et al., 2000, Cancer J Sci. Am. 6(Suppl 1):561-6; Cao et al., 1998, Stem Cells 16(Suppl 1):251-60; Kuiper et al., 2000, Adv. Exp. Med. Biol. 465:381-90). These molecules can be administered systemically to the host.

III. Methods of Use

A number of primary uses for the compounds of this disclosure are envisioned. The disclosed compositions are intended to be included in the routine immunization schedule of infants and children where *Burkholderia* is endemic and in individuals at risk for exposure to *Burkholderia*, such as travelers to areas where *Burkholderia* is found, or as individuals who work where *Burkholderia* is found or at risk of experiencing a bioterrorist attack. It is also intended to be used for intervention in epidemics caused by *Burkholderia*, including *B. pseudomallei* or *B. mallei*. The disclosed conjugates of the invention are also expected to be capable of inducing antibodies which may prevent, lessen or attenuate the severity, extent or duration of an infection by *Burkholderia*, including *B. mallei*, *B. pseudomallei*, *B. thailandensis* (although likely rare to occur) or a combination thereof.

In a particular example, methods are disclosed for treating a subject having melioidosis. In some embodiments, these methods include inducing an immune response to melioidosis to decrease a sign or symptom associated with melioidosis. In some examples, the disclosed method is used for treating a subject with acute melioidosis, such as during a bioterrorist attack. In some examples, the method is used for treating a subject with chronic melioidosis.

It is contemplate that a disclosed composition can be administered instead of or in addition to one or more additional known therapies for treatment of melioidosis. For example, additional therapies for acute melioidosis include intravenous ceftazidime for treatment of acute melioidosis. Meropenem, imipenem and cefoperazone-sulbactam (Sulperazone) are also active. Intravenous amoxicillin-clavulanate (co-amoxiclav) may also be used. Intravenous antibiotics are typically given for a minimum of 10 to 14 days, and are continued until the patient's temperature has returned to normal for more than 48 hours: it is not uncommon for patients to require parenteral treatment continuously for more than a month. Additional possible therapeutic agents for acute melioidosis include cefepime, ertapenem, piperacillin-sulbactam, doripenem and biapenem. Following the treatment of the acute disease, a maintenance treatment may be provided to the patient such as administration of co-trimoxazole and doxycycline.

The methods can include selecting a subject in need of treatment, such as a subject that exhibits one or more signs or symptoms known to one of skill in the art to be associated with melioidosis. Treatment of melioidosis includes reducing signs or symptoms associated with melioidosis. In some examples, a decrease or slowing melioidosis progression is an alteration of at least 10%, at least 20%, at least 50%, or at least 75%. In some examples, treatment using the methods disclosed herein prevent reoccurrence of melioidosis or the severity of melioidosis if it does reoccur.

In additional examples, methods are disclosed for treating a subject having glanders. For example, these methods include inducing an immune response to glanders to decrease a sign or symptom associated with glanders. The methods can include selecting a subject in need of treatment, such as a subject that exhibits one or more signs or symptoms known to one of skill in the art to be associated with glanders. Treatment of glanders includes reducing signs or symptoms associated with glanders. In some examples, a decrease or slowing glanders progression is an alteration of at least 10%, at least 20%, at least 50%, or at least 75%. In some examples, treatment using the methods disclosed herein prevent reoccurrence of glanders or the severity of glanders if it does reoccur.

Dosage for Vaccination

The disclosed compositions contains an effective, immunogenic amount of the disclosed CPS-protein immunogenic conjugates. In some embodiments, a disclosed CPS-protein immunogenic conjugate comprises purified 6-deoxyheptan capsular polysaccharide (CPS) from *B. pseudomallei*, *B. thailandensis* or *B. mallei* chemically activated and covalently linked to recombinant CRM197 diphtheria toxin mutant (CRM197) to produce CPS-CRM197. The effective amount of conjugate per unit dose sufficient to induce an immune response to *Burkholderia*, including *B. pseudomallei* or *B. mallei*, depends, among other things, on the species of mammal inoculated, the body weight of the mammal and the chosen inoculation regimen as is well known in the art. In some examples, inocula contain conjugates with concentrations of CPS of about 1 micrograms to about 100 milligrams per inoculation (dose), including about 2.5 micrograms to about 5 micrograms per dose, about 5 micrograms to about 50 micrograms, or about 2.5 micrograms to about 10 micrograms per dose, or about 2.5 micrograms to about 20 micrograms per dose. Such inocula would also contain concentrations of Hcp1 of about 1 micrograms to about 100 milligrams per inoculation (dose), including about 2.5 micrograms to about 5 micrograms per dose, about 5 micrograms to about 50 micrograms, or about 5 micrograms to about 10 micrograms per dose, or about 5 micrograms to about 20 micrograms per dose and/or concentrations of TssM of about 1 micrograms to about 100 milligrams per inoculation (dose), including about 2.5 micrograms to about 5 micrograms per dose, about 5 micrograms to about 50 micrograms, or about 5 micrograms to about 10 micrograms per dose, or about 5 micrograms to about 20 micrograms per dose. The term "unit dose" as it pertains to the inocula refers to physically discrete units suitable as unitary dosages for mammals, each unit containing a predetermined quantity of active material calculated to produce the desired immunogenic effect in association with the required diluent.

Inocula are typically prepared as a solution in a physiologically tolerable (acceptable) diluent such as water, saline or phosphate-buffered saline or other physiologically tolerable diluent to form an aqueous pharmaceutical composition. The route of inoculation may be intramuscular, subcutaneous and the like, which results in eliciting antibodies protective against *Burkholderia*, including *B. pseudomallei*, *B. mallei* and/or *B. thailandensis*. The dose is administered at least once. In order to increase the antibody level, one or more doses may be administered approximately 3 days to 1, 2, 3, 4, 5 or 6 weeks after the initial injection. Subsequent doses may be administered as indicated. Adjuvants, such as aluminum hydroxide, QS-21, TiterMax™ (CytRx Corp., Norcross Ga.), Freund's complete adjuvant, Freund's incomplete adjuvant, interleukin-2, thymosin, and the like, may also be included in the compositions.

The administration of the disclosed compositions may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided either prior to the anticipated exposure to *Burkholderia*, including *B. pseudomallei, B. mallei, B. thailandensis* or a combination thereof (so as to attenuate the anticipated severity, duration or extent of an infection and disease symptoms) or after the initiation of the infection.

For all therapeutic and prophylactic uses, the conjugates, compositions and other necessary reagents and appropriate devices and accessories may be provided in kit form so as to be readily available and easily used.

The following examples illustrate certain embodiments of the present disclosure, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLES

Example 1

Development of Subunit Vaccines that Provide High Level Protection and Sterilizing Immunity Against Acute Inhalational Melioidosis This example demonstrates the development of subunit vaccines that provide high level protection and sterilizing immunity against acute inhalational melioidosis.

*Burkholderia pseudomallei*, the etiologic agent of melioidosis, causes severe disease in humans and animals. Diagnosis and treatment of melioidosis can be challenging and no licensed vaccines currently exist. Studies have shown that this pathogen expresses a variety of structurally conserved protective antigens that include cell-surface polysaccharides and cell-associated/-secreted proteins. Based on this, such antigens have become important components of the subunit vaccine candidates which are disclosed herein. In the present study, the 6-deoxyheptan capsular polysaccharide (CPS) from *B. pseudomallei* was purified, chemically activated and covalently linked to recombinant CRM197 diphtheria toxin mutant (CRM197) to produce CPS-CRM197. Additionally, tandem nickel-cobalt affinity chromatography was used to prepare highly purified recombinant *B. pseudomallei* Hcp1 and TssM proteins. Immunization of C57BL/6 mice with CPS-CRM197 produced high-titer IgG and opsonizing antibody responses against the CPS component of the glycoconjugate while immunization with Hcp1 and TssM produced high titer IgG and robust IFN-$\gamma$ secreting T cell responses against the proteins. Extending upon these studies, we found that when vaccinated with a combination of CPS-CRM197 plus Hcp1, 100% of the mice survived a lethal inhalational challenge of *B. pseudomallei*. Remarkably, 70% of the survivors had no culturable bacteria in their lungs, livers or spleens indicating that the vaccine formulation had generated sterilizing immune responses. Collectively, these studies help to better establish surrogates of antigen-induced immunity against *B. pseudomallei* as well as provide valuable insights towards the development of a safe, affordable and effective melioidosis vaccine.

Materials and Methods

Bacterial strains, plasmids and growth conditions. Bacterial strains and plasmids used in this study are described in Table 1. *Escherichia coli* strains with plasmids were cultured on Luria Bertani-Lennox (LB; Fisherbrand) agar or in LB broth containing ampicillin (100 µg/ml). *B. pseudomallei* RR2683 was cultured in LB broth or on LB agar supplemented with thiamine (5 µg/ml) and adenine (100 µg/ml). *B. pseudomallei* K96243 was cultured in LB broth or on LB agar. All bacterial cultures were incubated at 37° C.; broth cultures were incubated with shaking (200 rpm). Bacterial stocks were maintained at −80° C. as 20% glycerol suspensions. All manipulations of *B. pseudomallei* K96243 were conducted in CDC/USDA approved and registered biosafety level 3 (BSL3) or animal biosafety level 3 (ABSL3) facilities at the University of South Alabama or the University of Texas Medical Branch, and experiments were performed in compliance with the rules and regulations of the U.S. Federal Select Agent Program.

TABLE 1

Bacterial strains and plasmids used in this study.

| Strains | Description[a] | Reference/source |
|---|---|---|
| *Escherichia coli* | | |
| TOP10 | Lab strain for cloning and protein expression | Life Technologies |
| *Burkholderia pseudomallei* | | |
| RR2683 | OPS-deficient derivative of the select agent excluded strain Bp82; ΔpurM, ΔrmlD | (61) |
| K96243 | Wild type; clinical isolate from Thailand | (62) |
| Plasmids | | |
| pBAD/HisA | Arabinose inducible, 6xHis-Tag expression vector; Ap[R] | Life Technologies |
| pBADBmhcp1-6HisF | pBAD/HisA containing *B. mallei* hcp1 (BMAA0742) with an N-terminal His-Tag | Pumpuang et al, 2017 |
| pMB1000 | pUC57Kan containing *B. pseudomallei* tssM (BPSS1512) corresponding to amino acids 191-474 in which the Cys codon (TG C) at position 102 in TssM has been changed to a Gly codon (GGC) | This study (GenScript) |

TABLE 1-continued

Bacterial strains and plasmids used in this study.

| Strains | Description[a] | Reference/source |
|---|---|---|
| pMB1001 | pBAD/HisA containing *B. pseudomallei* tssM (BPSS1512) corresponding to amino acids 191-474 in which the Cys codon (TGC) at position 102 in TssM has been changed to a Gly codon (GGC); N-terminal His-Tag | This study |

[a]Ap, ampicillin; R, resistant

CPS purification. Broth in 2 L baffled Erlenmeyer flasks was inoculated with *B. pseudomallei* RR2683 and incubated overnight at 37° C. with shaking (200 rpm). Cell pellets were obtained by centrifugation and extracted using a modified hot aqueous-phenol procedure (31). Purified CPS antigens were then obtained essentially as previously described (30, 56) which are hereby incorporated by reference in their entirety.

Glycoconjugate synthesis. Recombinant, pre-clinical grade CRM197 was purchased from Reagent Proteins. The CPS-CRM197 glycoconjugates used in this study were synthesized essentially as previously described (30, 56). Briefly, purified CPS was solubilized at 5 mg/ml in PBS (BupH; Pierce) and added to a small amber vial. To each ml of the CPS solution was added ~6 mg (~30 mM) of sodium meta-periodate. Once the crystals had dissolved, the reaction mixture was incubated for ~40 minutes at room temperature with stirring. To remove any excess oxidizing agent, the reaction mixture was applied to a Zeba Desalt Spin Column (Pierce) equilibrated with either PBS or BB (Pierce) and the eluate was collected. To facilitate conjugation of the CPS to the carrier protein (CRM197 buffer exchanged at 5 mg/ml into either PBS or BB on a Zeba column), the activated CPS was added to small amber vial. To each ml of the CPS solution was added 500 µl of the carrier protein (5 mg/ml stock). Following mixing by gentle agitation, 10 µl of a 1 M sodium cyanoborohydride stock (in 10 mM NaOH) was added to each milliliter of the conjugation mixture and the reaction incubated at 37° C. for 10 days with stirring. The conjugate reaction was then dialyzed against $dH_2O$ using a 3500 MWCO Slide-A-Lyzer cassette (Pierce), syringe filter (0.45 µM) sterilized and lyophilized. BCA assay (Pierce) was used to quantitate the protein concentration of the glycoconjugate stock (the remainder of the mass was assumed to be polysaccharide).

Protein expression and purification. Recombinant Hcp1 harboring an N-terminal 6×His-Tag was purified from *E. coli* TOP10 (pBADBmhcp1-6HisF) as previously described (33). For expression of recombinant TssM with an N-terminal 6×His-Tag, the tssM ORF (BPSS1512) in which the Cys codon (TGC) at position 102 in rTssM was changed to a Gly codon (GGC) was cloned into pBAD/HisA (34). Briefly, plasmid pMB1000 (synthesized at GenScript, Piscataway, N.J.) was digested with NcoI and HindIII to release the tssM-G102 insert which was then cloned into similarly digested pBAD/HisA to produce pMB1001. Recombinant DNA techniques were conducted as previously described (49). DNA sequencing was performed by ACGT Inc. TssM was purified from *E. coli* TOP10 (pMB1001) essentially as previously described for Hcp1 (33). The purity of Hcp1 and TssM was verified by SDS-PAGE. Protein concentrations were determined using a BCA protein assay kit (Pierce). Endotoxin removal was performed using High Capacity Endotoxin Removal Resin (Pierce) as per manufacturer's instructions. The amount of endotoxin in the Hcp1 and TssM preparations was quantitated using a LAL Chromogenic Endotoxin Quantitation Kit (Pierce) as per manufacturer's instructions. Syringe filter (0.45 µM) sterilized proteins were stored at 4° C.

SDS-PAGE and Western immunoblotting. Glycoconjugate samples were solubilized in 1×SDS-PAGE sample buffer and heated to 100° C. for 5 minutes prior to electrophoresis on 4-20% Tris-HEPES gels (Pierce). Proteins were visualized via staining with Coomassie Blue R-250. For Western immunoblot analyses, the glycoconjugate samples and controls were separated on the same 4-20% gels and electrophoretically transferred to nitrocellulose membranes. The membranes were blocked with 3% skim milk in high salt Tris-buffered saline (HS-TBS; 20 mM Tris, 500 mM NaCl, pH 7.5) for 60 minutes at room temperature and then incubated for 1 hour at room temperature with a 1/1000 dilution of a *B. pseudomallei* CPS-specific mAb (3C5) (57). To facilitate detection, the membranes were incubated for 1 hour at room temperature with 1/5000 dilutions of an anti-mouse IgG horse radish peroxidase conjugate (SouthernBiotech). Blots were visualized using Pierce ECL Western Blotting Substrate (Thermo Scientific) and a ChemiDoc XRS imaging system (BioRad).

Mouse immunizations. Groups of 6-8 week-old female C57BL/6 mice (n=16 per group; Charles River) were immunized subcutaneously on days 0, 21 and 35 with the following antigens: CPS-CRM197 (2.5 µg/dose of CPS as a conjugate), Hcp1 (5 µg/dose), TssM (5 µg/dose), CPS-CRM197 plus Hcp1, or CPS-CRM197 plus TssM. All antigens were formulated in tissue culture grade PBS pH 7.2 (Gibco) with Alhydrogel 2% (500 µg/dose; Brenntag) and CpG (20 µg/dose; ODN 2006, InvivoGen) as the adjuvant system. Mice immunized with adjuvant only served as controls.

Analysis of antibody titers. Terminal bleeds (n=6 mice per group) were conducted one week after the final boost. Serum was stored at −80° C. until required for use. Antibody responses directed against the vaccine antigens were assessed by ELISAs essentially as previously described (30, 58). Briefly, 96 well Maxisorp plates (Nunc) were coated overnight at 4° C. with purified CPS, Hcp1 or TssM (1 µg/ml) solubilized in carbonate buffer (pH 9.6). The plates were blocked at room temperature for 30 min with StartingBlock T20 (TBS) Blocking Buffer (Pierce) and then incubated for 2 h at 37° C. with the mouse serum samples serially diluted in Tris-buffered saline+0.05% Tween 20 (TBS-T; pH 7.5)+10% StartingBlock T20. To facilitate detection, the plates were incubated for 1 h at 37° C. with 1/2000 dilutions of anti-mouse IgM, IgG, IgG1 or IgG2b horse radish peroxidase conjugates (SouthernBiotech). The plates were developed with TMB substrate (KPL) and read at 620 nm using a FLUOstar Omega microplate reader (BMG Labtech). The reciprocals of the highest dilutions exhibiting ODs that were 3× background levels were used to determine the endpoint titers for the individual mice.

Opsonophagocytosis assays. The murine macrophage cell line RAW 264.7 (ATCC TIB-71) was maintained in Dulbecco's modified Eagle's medium supplemented with 10% (v/v) HI fetal bovine serum (DMEM-10; Invitrogen) and a standard mixture of antibiotics (100 U/ml penicillin, 100 μg/ml streptomycin and 250 μg/ml amphotericin B; Sigma) at 37° C. under an atmosphere of 5% $CO_2$. Opsonophagocytosis assays were performed essentially as previously described (30, 59). Briefly, RAW 264.7 cells resuspended in DMEM-10 were transferred into 24-well tissue culture plates at a density of $1×10^6$ cells/well and incubated overnight. *B. pseudomallei* K96243 cultures grown to early-log phase were pelleted, resuspended at a density of $1×10^6$ CFU/ml in DMEM or DMEM containing 1% adjuvant only, Hcp1, TssM, CPS-CRM197, CPS-CRM197 plus Hcp1 or CPS-CRM197 plus TssM mouse immune serum (pooled and HI for 30 minutes at 56° C.) and then incubated at 37° C. for 1 h. RAW 264.7 monolayers were washed twice with Hanks' Balanced Salts Solution (HBSS; Invitrogen) prior to the addition of the opsonized bacterial suspensions. The monolayers were incubated with the bacteria for 1 h at 37° C. under an atmosphere of 5% $CO_2$ and then washed twice with HBSS to remove extracellular bacteria. Infected RAW 264.7 cells were incubated with fresh DMEM-10 containing 250 μg/ml kanamycin to suppress the growth of residual extracellular bacteria. At 3 h post-infection, the infected monolayers were washed twice with HBSS, lysed with 0.2% (v/v) Triton X-100 (Sigma) and serial dilutions of the lysates were plated onto LB agar plates and incubated at 37° C. for 48 h. Plate counts were used to enumerate bacterial loads.

ELISpot assays. Spleens (n=4 per group) were harvested one week after the final boost from terminally bled mice. Single cell suspensions were prepared by passing the organs through 70 μm cell strainers (Falcon) into RPMI-1640 (Gibco) supplemented with 10% HI fetal bovine serum and 1× Penicillin/Streptomycin (Gibco) (RPMI-10). Cells were pelleted by centrifugation (500×g), resuspended in Red Blood Cell Lysis Solution (Sigma), incubated at room temperature for 10 minutes, pelleted (500×g) and then resuspended in RPMI-10 at a concentration of $5×10^6$ cells/ml. Mouse IFN-gamma ELISpot Kits (R&D Systems) were used per the manufacturer's instructions. Splenocytes stimulated with CPS-CRM197, Hcp1, TssM or media only were added to the plates at a concentration of $2.5×10^5$ cells/well and then incubated for 48 hours at 37° C. under an atmosphere of 5% $CO_2$. The ELISpot plates were processed and developed per the manufacturer's instructions. Plates were imaged using an ImmunoSpot 51 Analyzer (Cellular Technology Ltd.). IFN-γ secreting T cells were quantitated using ImmunoSpot v5.1 Professional DC Smart Count software (Cellular Technology Ltd.).

$LD_{50}$ determination. Groups of 16-18 week-old, female C57BL/6 mice (Charles River Laboratories) were housed in standard micro-isolator cages and were provided water and food ad libitum. Mice were acclimated to housing for at least seven days prior to bacterial infection. The $LD_{50}$ for *B. pseudomallei* K96243 was determined by exposing three groups of mice (n=6 to 8 mice/group) to 67, 728 and 53,500 CFU as previously described (59). Mice were monitored for survival over 35 days and the $LD_{50}$ calculated using methods described by Reed and Muench (60).

Mouse challenge studies. Five weeks after the final boost (day 70), the remainder of the immunized mice (n=10 per group) were challenged with *B. pseudomallei* K96243 at a nebulizer concentration of ~$4.65×10^7$ CFU/ml via aerosol essentially as previously described (59). Briefly, three groups of 20 mice were exposed to aerosolized bacteria via a three-jet collision nebulizer for 15 min at a constant flow rate of 30 L/min. During this automated aerosol exposure, animals were restrained in a Biaera plastic aerosol rodent exposure box housed within a Class III biological safety cabinet in a biosafety level-3 suite using an automated aerosol exposure system. Animals were placed inside nose-only exposure restraint cones (In-Tox products L.L.C, Moriarty, N. Mex.). Nebulizers were filled with 10 ml of LB broth containing the appropriate concentration of bacteria. Doses presented (Dp) to each group of animals were determined by performing standard CFU counts on the samples collected from an all-glass impinger (SKC BioSampler; SKC Inc., Eighty-Four, Pa.) containing LB broth with 4% glycerol and approximately 20 μl of antifoam 204 (Sigma Aldrich). The Dp was calculated using the following formulas: Dp (CFU)=$C_{Aero}$ (CFU/ml)×exposure time (min)×minute volume (ml); minute volume=2.1(weight [g])$^{0.75}$. Weight and survival of the challenged mice were monitored for 35 days. Humane endpoints were strictly observed via daily monitoring throughout the study. Mice in the three challenge groups received Dp=1590, 1650 and 1550 CFU which correlated to 10.3, 10.7 and 10.1 $LD_{50s}$, respectively.

CFU enumeration and histological evaluation. At 35 days post-challenge, surviving animals were euthanized and their lungs, livers and spleens collected for CFU enumeration and histopathology. Half of each organ was fixed in 10% normal buffered formalin and the remaining half was weighed and homogenized using Covidien Precision tissue grinders (Fisher Scientific). Tissue homogenates were serially diluted in PBS, plated, and incubated for 48 hours at 37° C. Colonies were counted and normalized to organ weight (g). For histopathological analysis, fixed tissues were embedded in paraffin and sectioned prior to staining with Hematoxylin and Eosin (H&E). Pathology scoring was performed as previously described (59).

Statistical analysis. All graphs were produced by using GraphPad Prism 7.03 (GraphPad Software Inc.). Opsonophagocytosis and ELISpot data was analyzed using a Mann-Whitney U test. Survival data was analyzed using a log-rank (Mantel-Cox) test.

Results

Figure 1A:
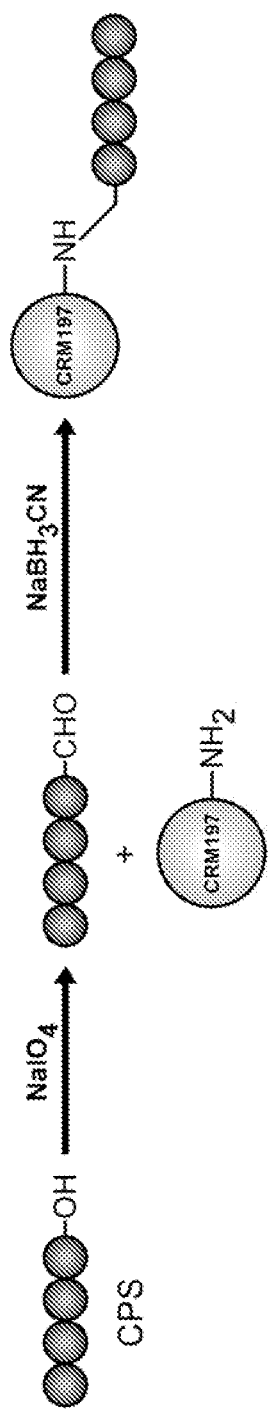
FIGS. 1A-1B Synthesis and physical analysis of CPS-CRM197.
Figure 1B:
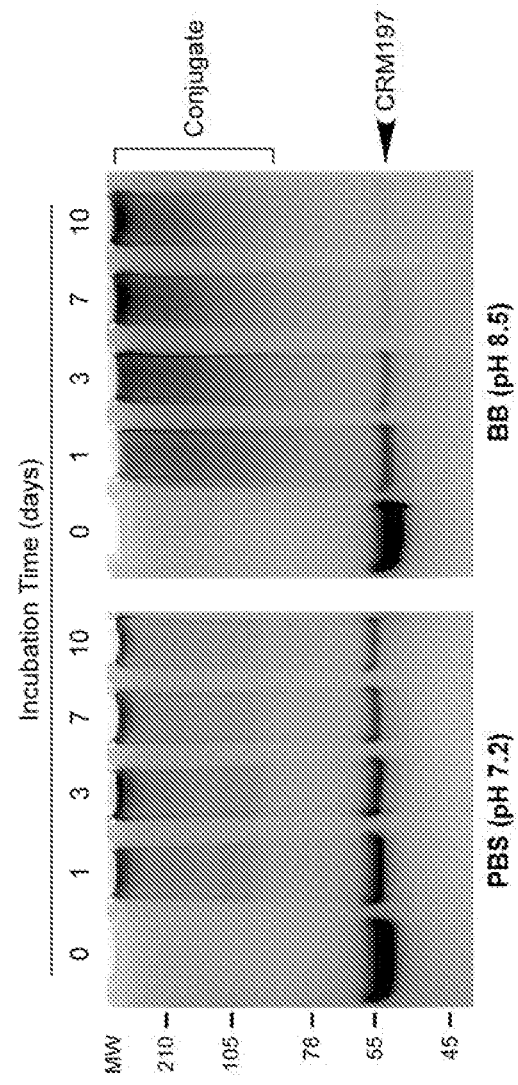
Figure 3A:
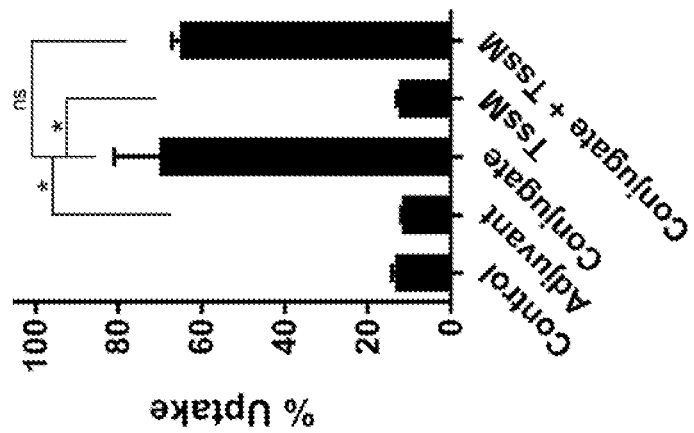
FIGS. 3A-3B. Functional analysis of antibody responses raised against CPS-CRM197, Hcp1 and TssM. C57BL/6 mice (n=6 per group) were immunized on days 0, 21 and 35 with adjuvant only (Alhydrogel/CpG), conjugate only, Hcp1 only, TssM only, conjugate plus Hcp1 and conjugate plus TssM. Immune serum samples were collected on day 42. *B. pseudomallei* K96243 was incubated with (FIG. 3A) media only (no serum control), pooled HI adjuvant (Alhydrogel/CpG) only immune serum, pooled HI conjugate only immune serum, pooled HI Hcp1 only immune serum, pooled HI conjugate plus Hcp1 immune serum or (FIG. 3B) media only (no serum control), pooled HI adjuvant (Alhydrogel/CpG) only immune serum, pooled HI conjugate only immune serum, pooled HI TssM only immune serum, pooled HI conjugate plus TssM immune serum. Following incubation for 1 hour, opsonized bacteria were added to RAW 264.7 murine macrophage monolayers. Uptake was quantitated at 3 hours post-infection. Values represent the means±SD of three individual assays conducted in triplicate. Figures are representative of at least three independent experiments conducted on different days. HI=heat inactivated; Conjugate=CPS-CRM197; ns=not significant; *=(P<0.05).
Figure 3B:
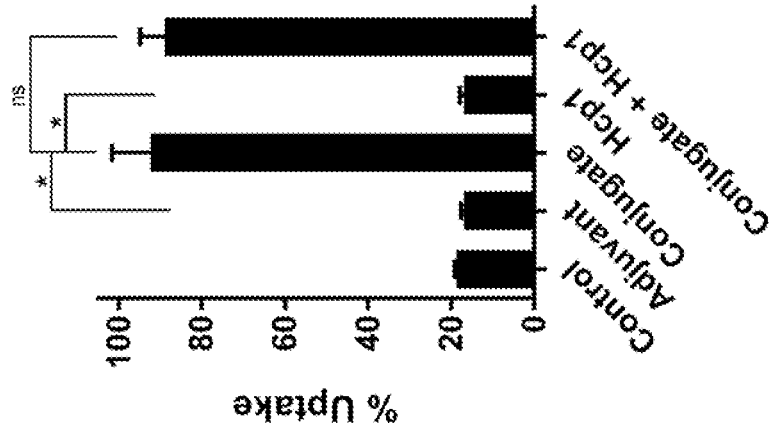
Figure 4A:
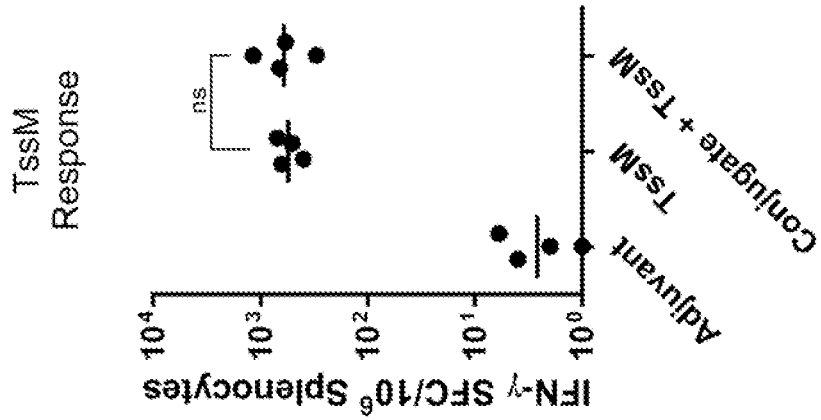
FIGS. 4A-4C. Characterization of cellular immune responses raised against CPS-CRM197, Hcp1 and TssM. C57BL/6 mice (n=4 per group) were immunized on days 0, 21 and 35 with adjuvant only (Alhydrogel/CpG), conjugate only, Hcp1 only, TssM only, conjugate plus Hcp1 and conjugate plus TssM. Spleens were harvested on day 42 and IFN-γ secreting T cell responses against (FIG. 4A) CPS-CRM197, (FIG. 4B) Hcp1 and (FIG. 4C) TssM were quantitated by ELISpot. Black dots represent the means of assays conducted in duplicate for individual mice. Black bars represent geometric means for a group. Conjugate=CPS-CRM197; SFC=spot forming cells; ns=not significant; *=(P<0.05).
Figure 4B:
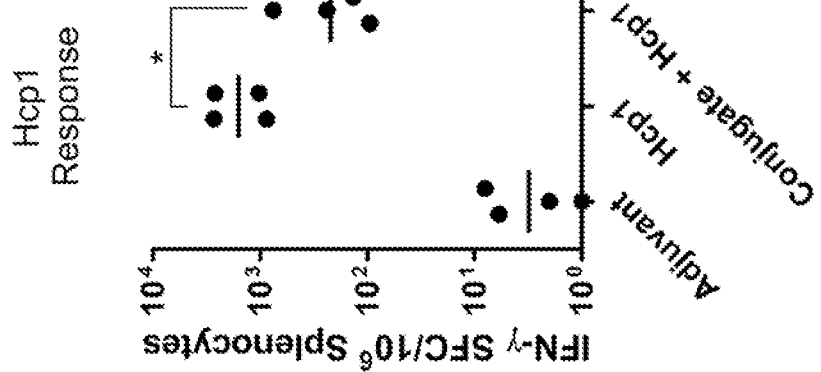
Figure 4C:
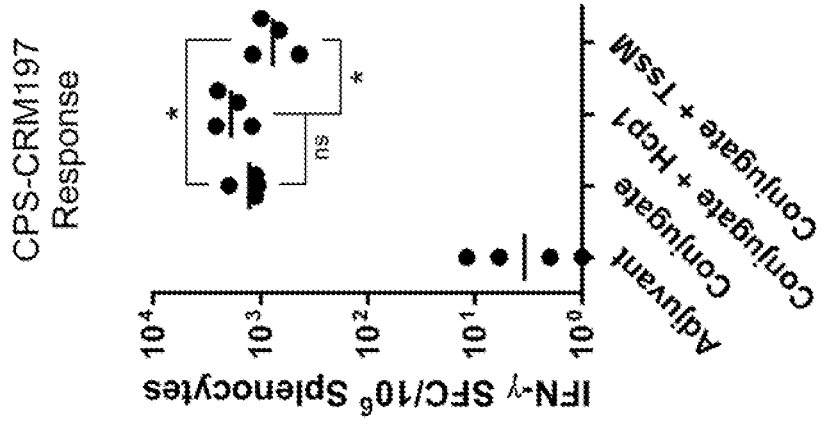
Figure 6:
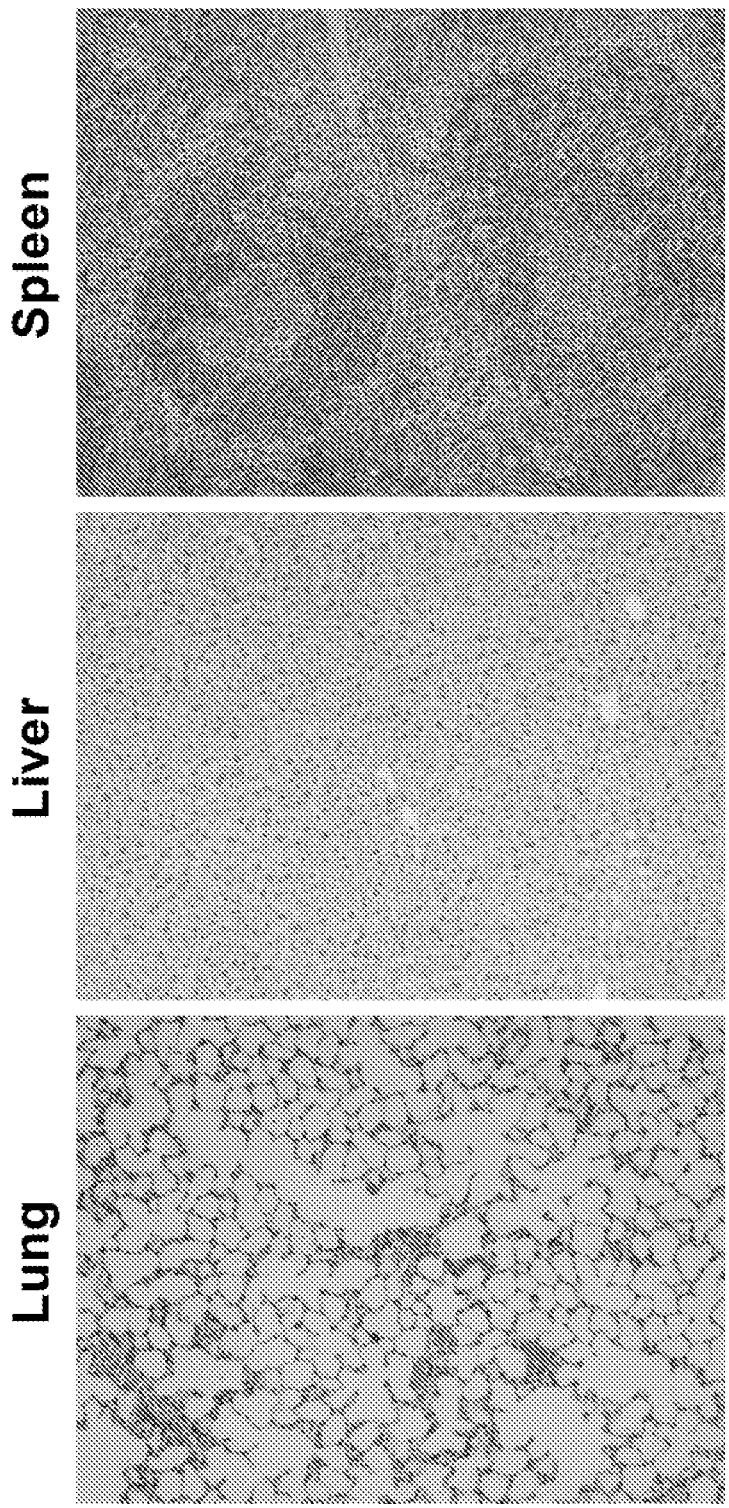
FIG. 6. Histopathological analysis of mouse tissues following a lethal inhalational challenge with *B. pseudomallei*. Following termination of the challenge study, lungs, livers and spleens were harvested from five (mouse #1-5) of the ten survivors that had been immunized with CPS-CRM197 plus Hcp1. The tissues were fixed and stained by H&E. Images are representative of all 5 mice (original magnification, 400×).
Figure 7:
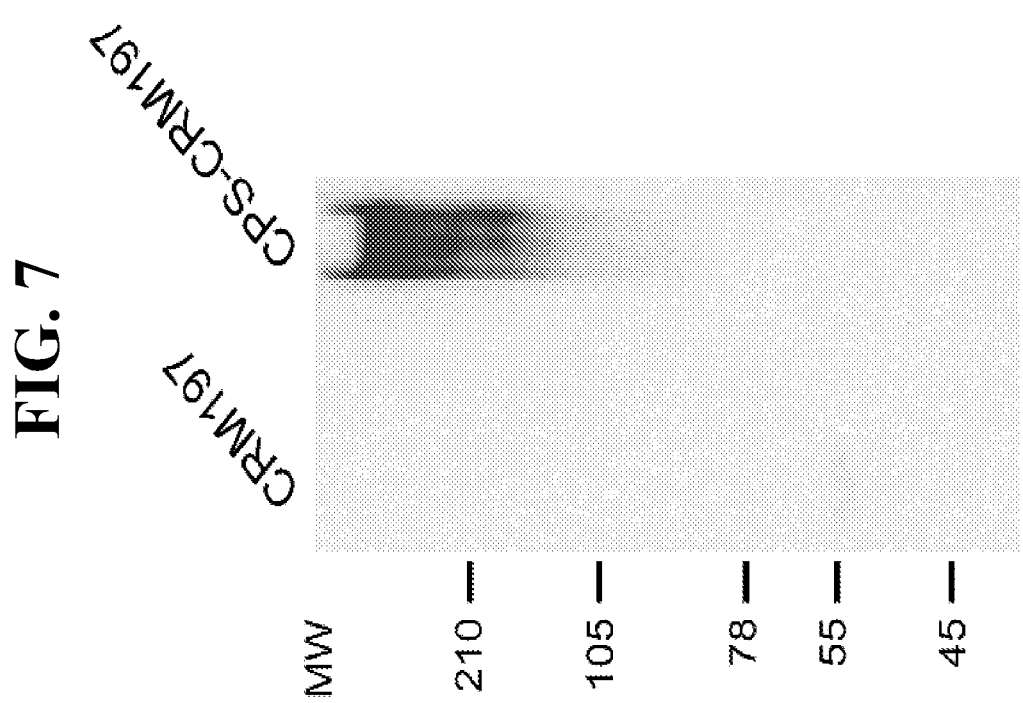
FIG. 7. Western immunoblot analysis of CPS-CRM197. CRM197 (control) and CPS-CRM197 were separated on a 4-20% Tris-HEPES gel and electrophoretically transferred to a nitrocellulose membrane. CPS was detected using the *B. pseudomallei* CPS-specific mAb, 3C5 (see Examples). The positions of the protein molecular standards (kDa) are indicated on the left.
Figure 8:
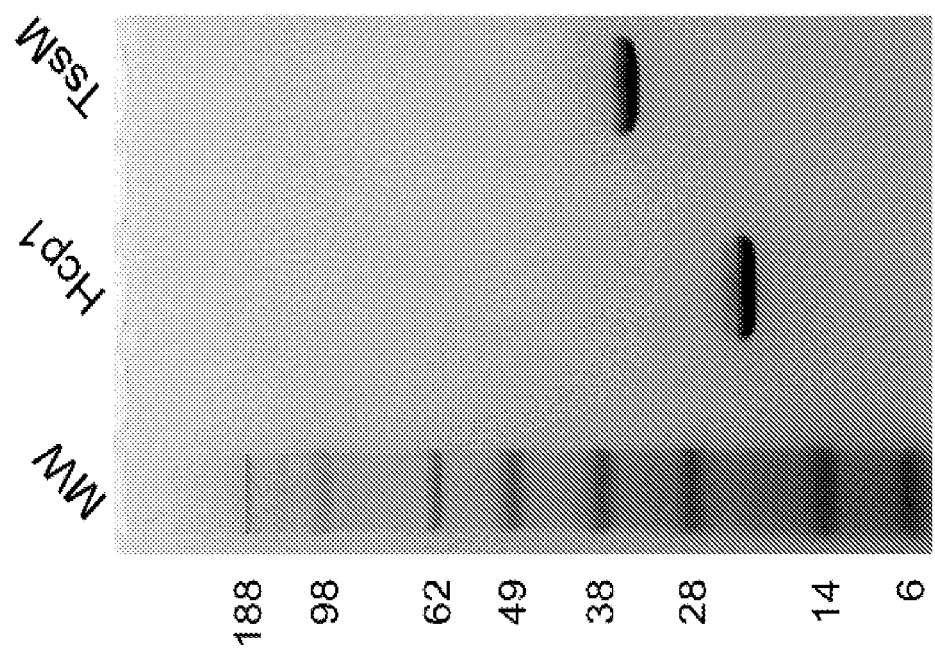
FIG. 8. SDS-PAGE analysis of recombinant *B. pseudomallei* Hcp1 and TssM antigens. Hcp1 and TssM were separated on a 4-12% Bis-Tris Bolt gel and visualized with Coomassie Blue R-250 (see Materials and Methods). The protein molecular standards (kDa) are indicated on the left.
Figure 9:
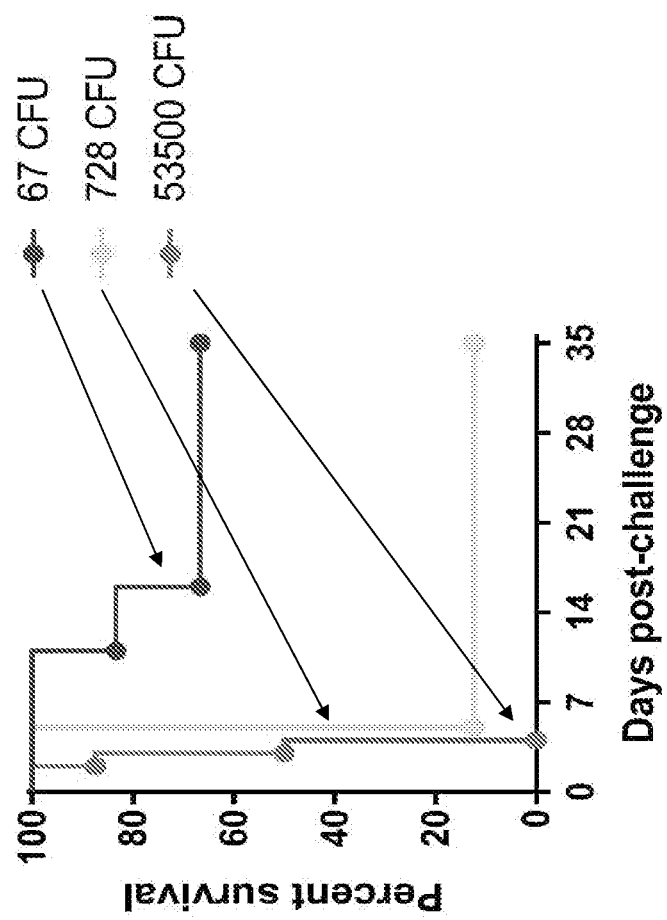
FIG. 9. Determination of the inhalational $LD_{50}$ of *B. pseudomallei* K96243 for C57BL/6 mice. Groups of 16-18 week-old, female C57BL/6 mice (n=6 to 8 mice/group) were exposed to 67, 728 and 53,500 CFU of *B. pseudomallei*

Synthesis of CPS-CRM197. To construct the glycoconjugate material used in this study, the 6-deoxyheptan CPS from *B. pseudomallei* RR2683 (select agent excluded strain) was isolated using a hot aqueous-phenol extraction method (30, 31). The purified CPS was then oxidized and covalently linked to CRM197 diphtheria toxin mutant (CRM197) via reductive amination to produce CPS-CRM197 (FIG. 1a). To optimize conjugation of the CPS to CRM197, small scale reactions (5 mg CPS+2.5 mg CRM197) were initially conducted in phosphate buffered saline pH 7.2 (PBS) or borate buffer pH 8.5 (BB). At various time points during the coupling reactions, samples were drawn and examined by SDS-PAGE (FIG. 1b). As indicated by shifts in molecular weights of the conjugate material relative to CRM197 controls, results demonstrated that the CPS covalently linked to the carrier protein in a time-dependent manner. Reaction of the CPS with CRM197 was found to be most efficient in BB with the majority of the carrier protein being coupled by day 10. Interestingly, while the conjugate material synthesized in BB was isolated in a soluble form, most of the conjugate material produced in PBS ended up as an insoluble precipitate. Based on these observations, a large-scale reaction of CPS (20 mg) with CRM197 (10 mg) was conducted using BB as the solvent system. Upon termination of the reaction, the yield of CPS-CRM197 was determined to be 23.3 mg (~77% of the starting material). Analysis of the glycoconjugate material revealed that it contained 60% (w/w) CPS and 52 EU/mg as determined by protein and endotoxin assays, respectively. Similar to previous studies, Western immunoblotting confirmed that the structural integrity/antigenicity of the CPS remained intact following chemical activation and linkage to the carrier protein based upon strong reactivity with mAb 3C5 (FIG. S1) (30).

Production of recombinant Hcp1 and TssM. To obtain recombinant Hcp1 and TssM for use in the present study, N-terminal His-tagged versions of these proteins were expressed and purified from *E. coli*. Like our previous studies, the Hcp1 and TssM antigens were extracted from whole cell pellets in a soluble form and purified to homogeneity using tandem nickel-cobalt chromatography (32-34). SDS-PAGE was used to assess the purity and structural integrity of the antigens (FIG. 8). Endotoxin concentrations associated with the Hcp1 and TssM preparations were 0.20 and 0.49 EU/mg, respectively, as determined by LAL assay.

Analysis of antibody responses raised against CPS-CRM197, Hcp1 and TssM. To assess the immunogenic potential of our vaccine antigens, groups of C57BL/6 mice were immunized with i) adjuvant only, ii) CPS-CRM197, iii) Hcp1, iv) TssM, v) CPS-CRM197 plus Hcp1 or vi) CPS-CRM197 plus TssM. One week after the final boost, serum was collected from the mice and antigen-specific IgM and IgG titers were determined by ELISA. As expected, the conjugate (whether alone or in combination with Hcp1 or TssM) stimulated the production of high titer IgM (endpoint titers$\geq 10^3$) and total IgG (endpoint titers$\geq 10^5$) responses against CPS (FIG. 2*a*). Similarly, the recombinant *Burkholderia* proteins (whether alone or in combination with CPS-CRM197) stimulated the production of high titer IgM (endpoint titers$\geq 10^3$) and total IgG (endpoint titers$\geq 10^6$) responses against Hcp1 and TssM (FIGS. 2*b* and 2*c*). Additionally, analysis of the immune serum samples revealed that balanced Th2/Th1 type responses were raised against all antigens as determined by IgG1:IgG2b ratios (FIGS. 2*a-c*) (35, 36).

To assess the functionality of the CPS- and protein-specific antibodies, opsonophagocytosis assays were conducted. As shown in FIG. 3, pre-incubation of *B. pseudomallei* K96243 with heat-inactivated (HI) pooled antiserum from CPS-CRM197, CPS-CRM197 plus Hcp1 or CPS-CRM197 plus TssM immunized mice significantly enhanced bacterial uptake (>5-fold) into RAW264.7 cells compared to non-conjugate antiserum controls. When serum obtained from the adjuvant only, Hcp1 or TssM immunized mice was evaluated in the same assays, no differences in uptake levels were observed in comparison to the media only controls. Taken together, these results demonstrate that the conjugate material used in our vaccine formulations was capable of stimulating opsonizing antibody responses in C57BL/6 mice.

Analysis of cellular immune responses against CPS-CRM197, Hcp1 and TssM. One week after the final boost, single cell suspensions were prepared from the spleens of immunized mice and restimulated with the various vaccine antigens. ELISpot assays were then used to analyze T cell responses. Since CRM197 is a well-characterized T cell-dependent antigen, splenocytes isolated from mice immunized with CPS-CRM197, CPS-CRM197 plus Hcp1 or CPS-CRM197 plus TssM were restimulated with CPS-CRM197 for control purposes (37, 38). As shown in FIG. 4*a*, all conjugate-immunized mice exhibited robust IFN-γ secreting T cells responses when compared to the adjuvant only mice. Similarly, splenocytes obtained from mice immunized with the *Burkholderia* proteins (whether alone or in combination with CPS-CRM197) also exhibited robust IFN-γ secreting T cells responses when restimulated with Hcp1 or TssM, respectively (FIGS. 4*b* and 4*c*). Interestingly, when compared to one another, not all the immunized groups of mice displayed equivalent responses. For instance, when restimulated with conjugate material, splenocyte preparations from the CPS-CRM197 plus TssM group had significantly lower numbers of IFN-γ secreting T cells than the CPS-CRM197 or CPS-CRM197 plus Hcp1 immunized mice (FIG. 4*a*). Furthermore, when splenocytes from the CPS-CRM197 plus Hcp1 immunized mice were restimulated with Hcp1, fewer numbers of IFN-γ secreting T cells were detected compared to Hcp1 only immunized mice (FIG. 4*b*). No significant differences were observed, however, between the T cell responses obtained for the CPS-CRM197 plus TssM and TssM only immunized mice when restimulated with TssM (FIG. 4*c*). Collectively, these findings demonstrate that robust IFN-γ secreting T cell responses can be raised against the *Burkholderia* protein antigens used in this study.

Animal challenge studies. The ultimate goal of this study was to assess the ability of the various antigens to protect immunized mice against a lethal bacterial challenge. To facilitate this, we first had to establish a median lethal dose ($LD_{50}$) for our *B. pseudomallei* isolate using appropriately aged mice. This was accomplished by challenging 16-18-week-old C57BL/6 mice with varying doses of *B. pseudomallei* K96243 via an inhalational route and monitoring their survival for 35 days (FIG. S3). Upon termination of the experiment, we calculated the $LD_{50}$ to be 154 colony forming units (CFU). Once this had been accomplished, immunized mice were challenged with ~10 $LD_{50}$ of K96243 five weeks after the final boost and monitored for signs of morbidity and mortality over a 35 day period. As expected, all mice in the adjuvant only group succumbed rapidly to infection (≤8 days). In contrast, groups immunized with CPS-CRM197 (whether alone or in combination with Hcp1 or TssM) exhibited survival curves that were significantly different from the adjuvant control (FIGS. 5*a* and 5*b*). Specifically, immunization of mice with CPS-CRM197 plus Hcp1 resulted in 100% survival while immunization with CPS-CRM197 plus TssM or CPS-CRM197 alone resulted in 80% and 67% survival, respectively. Interestingly, only 30% and 20% of the mice immunized with Hcp1 or TssM, respectively, survived the full duration of the study.

To further investigate the protective capacity of our vaccine formulations, survivors were culled at day 35, and their lungs, livers, and spleens plated to quantitate bacterial loads.

As shown in FIG. 5c, 7/10 of the mice immunized with CPS-CRM197 plus Hcp1 had no culturable bacteria in any of their tissues. Interestingly, while mouse #2 from this group was shown to have high bacterial loads in its lungs, there was no evidence of dissemination to its liver or spleen. Results also demonstrated that 5/8 of the CPS-CRM197 plus TssM and 4/6 of the CPS-CRM197 immunized mice had no detectable bacteria in their tissues. Remarkably, no bacteria were isolated from the spleens of any of the mice. Consistent with these findings, histopathological analyses revealed that the lungs, livers and spleens from survivors in the CPS-CRM197 plus Hcp1 immunized group (mouse #1-5) were unremarkable and presented as normal healthy tissue with normal architecture (FIG. 6 and Table 2). Taken together, these studies demonstrate the vaccinogenic potential of our antigen formulations. Additionally, they show that immunization of C57BL/6 mice with CPS-CRM197 plus Hcp1 results in 100% survival and 70% sterilizing immunity following an acute inhalational challenge with B. pseudomallei.

TABLE 2

Histopathological analysis of mouse tissues following a lethal inhalational challenge with *B. pseudomallei*.

| Specimen Name | Grade* | Granulomas** | Lobar Pneumonia** |
|---|---|---|---|
| Mouse 1 - Lung | 0 | 0 | No |
| Mouse 1 - Liver | 0 | 0 | — |
| Mouse 1 - Spleen | 0 | 0 | — |
| Mouse 2 - Lung | 0 | 0 | No |
| Mouse 2 - Liver | 0 | 0 | — |
| Mouse 2 - Spleen | 0 | 0 | — |
| Mouse 3 - Lung | 0 | 0 | No |
| Mouse 3 - Liver | 0 | 0 | — |
| Mouse 3 - Spleen | 0 | 0 | — |
| Mouse 4 - Lung | 0 | 0 | No |
| Mouse 4 - Liver | 0 | 0 | — |
| Mouse 4 - Spleen | 0 | 0 | — |
| Mouse 5 - Lung | 0 | 0 | No |
| Mouse 5 - Liver | 0 | 0 | — |
| Mouse 5 - Spleen | 0 | 0 | — |

*Histopathology Grading System: 0 = no lesions, 0% of the tissue is affected; 1 = minimal change, 10% and less of the tissue is affected; 2 = mild change, 10-25% of the tissue is affected; 3 = moderate change, 25-50% of the tissue is affected; 4 = marked change, 50-75% of the tissue is affected; 5 = severe change, greater than 75% of the tissue is affected.

**Additional features evaluated: Number of large granulomas (>500 microns); Lobar pneumonia (Yes/No).

Discussion

Melioidosis is being increasingly recognized as an important cause of morbidity and mortality worldwide, yet no licensed vaccines currently exist to prevent disease in humans or animals (1, 16). Since *B. pseudomallei* is a facultative intracellular pathogen, protective immunity is likely complex requiring a combination of humoral and cell mediated responses. To address this, studies in our laboratories have been focused on the development of subunit vaccines that incorporate a combination of protective polysaccharide and protein antigens (26, 29). The rationale for this approach is that, when appropriately adjuvanted, such vaccines should be able to stimulate both protective antibody and T cell responses. Additionally, since these types of vaccines are antigenically defined, they can be designed to minimize safety issues and undesirable side-effects often associated with the use of whole cell or live attenuated vaccines. In the present study, we provide strong evidence that our subunit vaccines can protect mice against an acute inhalational challenge of *B. pseudomallei*. Collectively, our results help to better establish surrogates of antigen-induced immunity against this important bacterial pathogen as well as provide valuable insights towards the development of an antigenically defined, safe, affordable and effective melioidosis vaccine (39).

The 6-deoxyheptan CPS is an attractive vaccine candidate because it is i) a requisite virulence factor, ii) structurally conserved and iii) expressed by all known virulent isolates of *B. pseudomallei* (40). Additionally, several passive and active immunization studies have proven it to be a protective antigen (21, 28). Notably, we have previously shown that immunization of BALB/c mice with a CPS-cBSA conjugate provides significant protection against lethal intraperitoneal challenges of *B. pseudomallei* (26). While this study was an important first step in demonstrating the vaccinogenic potential of CPS, we recognized that there were limitations regarding the use of animal proteins to develop human vaccines. In the present study, therefore, we wanted to identify a carrier that would facilitate efficient production of a CPS-based glycoconjugate but, unlike cBSA, would also be licensable for use in humans.

There are five different carrier proteins currently used to produce human glycoconjugate vaccines: tetanus toxoid (T), meningococcal outer membrane protein complex (OMPC), *Haemophilus influenzae* protein D (HiD), diphtheria toxoid (D) and CRM197 (41). Of these, CRM197 is considered the most versatile since it has multiple lysyl side chains that are available for coupling with activated polysaccharides (41). Based on this, we elected to produce our conjugates using recombinant CRM197 (38). Initial attempts to conjugate CPS to CRM197 using PBS as a solvent system resulted in less than optimal conjugation and the formation of insoluble precipitates. To resolve these issues, we switched to a BB solvent system which resulted in high efficiency coupling and the production of soluble conjugate material that could be filter sterilized (42).

Capsular polysaccharides enable many bacterial pathogens to evade uptake and killing by phagocytic cells (43). CPS-based glycoconjugate vaccines can induce opsonizing antibody responses to combat disease caused by such organisms (44, 45). The intended purpose of the glycoconjugate material in our vaccine formulations, therefore, was to stimulate the production of opsonizing antibody responses against the CPS antigen. When immunized with CPS-CRM197, either alone or in combination with Hcp1 or TssM, C57BL/6 mice were found to generate high titer CPS-specific IgG responses. Such findings are consistent with previous studies using CPS-cBSA as an immunogen and confirmed that T cell-dependent type antibody responses were being raised against the polysaccharide portion of CPS-CRM197 (46). Extending upon these findings, we also investigated the opsonizing capacity of the immune serum samples. Results demonstrated that CPS-specific antibodies, whether alone or in combination with Hcp1- or TssM-specific antibodies, were functional and promoted uptake of *B. pseudomallei* into RAW 264.7 cells. These finding are consistent with several previous studies demonstrating that CPS-specific monoclonal antibodies and/or polyclonal antiserum enhance uptake of *B. pseudomallei* and/or *B. mallei* into phagocytic cells (28, 30, 47, 48).

A variety of proteins have been explored for their vaccinogenic potential in animal models of melioidosis. Varied results have been achieved, with no single antigen providing high level protection against acute challenges of *B. pseudomallei* (16). Recently, we demonstrated that when BALB/c mice were immunized with a combination of CPS-cBSA and recombinant LolC, rather than with CPS-cBSA or LolC individually, they exhibited higher survival rates when challenged with a lethal dose of *B. pseudomallei* (26). In the present study, we extended upon this finding by investigating the protective capacity of two different *Burkholderia* proteins combined with CPS-CRM197 in C57BL/6 mice. The proteins selected for this purpose were Hcp1 and TssM. Hcp1 is a major structural component of the virulence-associated *B. pseudomallei* type VI secretion system and is expressed in high levels upon activation of this system (32, 49). TssM is a potent deubitiquitinase involved in modulating host immune responses and is secreted by *B. pseudomallei* in a type II secretion system dependent manner (34, 50). These proteins were chosen because i) they are highly conserved amongst *B. pseudomallei* isolates, ii) they are known to be expressed in humans during active infections with the organism and iii) Hcp1 is a known protective antigen in animal models of experimental melioidosis (32, 51). In addition to these important attributes, recombinant Hcp1 and TssM are both well-behaved proteins that can be expressed at high levels in *E. coli*, purified in a soluble form and are stable for extended periods of time when stored at 4° C. (data not shown). When immunized with recombinant Hcp1 or TssM, either alone or in combination with CPS-CRM197, C57BL/6 mice were found to produce high titer IgG responses (endpoint titers≥$10^6$) against the proteins. Such results indicate that Hcp1 and TssM are highly immunogenic antigens.

Since *B. pseudomallei* is a capable of surviving and replicating within host cells, it is reasonable to predict that cell-mediated immune responses will be important for controlling infections caused by this pathogen. For instance, *B. pseudomallei* protein-specific IFN-γ secreting T cells will likely be required to promote efficient clearance of the organism following uptake by macrophages. Supporting this, recent studies have demonstrated a correlation between survival of melioidosis patients and enhanced T cell immunity to specific *B. pseudomallei* antigens (52, 53). Thus, the intended purpose of the *Burkholderia* proteins in our vaccine formulations was to stimulate the production of Hcp1- and TssM-specific IFN-γ secreting T cell responses. Results of ELISpot assays demonstrated that robust IFN-γ secreting T cell responses were observed in both Hcp1- and TssM-immunized mice. Interestingly, when Hcp1 was combined with CPS-CRM197, the Hcp1-specific T cell responses were significantly lower than those associated with Hcp1 only immunized mice. At present, the reason for this phenomenon is unclear. Further studies will be required to better understand this effect as well as determine whether or not it may be influencing vaccine efficacy. In addition to this, studies will be required to confirm which T cell populations (i.e. $CD4^+$, $CD8^+$ or both) are being activated by the *Burkholderia* proteins as well as what role(s) they might be playing in controlling *B. pseudomallei* infections.

Following three doses of the vaccine formulations, C57BL/6 mice were challenged with lethal inhalational doses (~10 $LD_{50}$) of *B. pseudomallei* K96243. This challenge route was chosen to evaluate the protective capacity of our vaccine antigens since it represents a natural route of infection and would also be the most likely mode of exposure in the event of a deliberate release of the organism (54). When used alone, Hcp1 and CPS-CRM197 were shown to provide varying degrees of protection (30% and 67% survival, respectively). Supporting our hypothesis that optimal protection likely requires both humoral and cellular immune responses, combining the antigens yielded an observable synergistic effect. Specifically, 100% of the mice immunized with CPS-CRM197 plus Hcp1 survived the full duration of the study. Although protection afforded by the antigen combination was not statistically different than CPS-CRM197 alone, there was a clear biological advantage associated with the use of this formulation. A major challenge in developing vaccines to combat disease caused by facultative intracellular pathogens is the ability to achieve sterilizing immunity (16, 55). Based upon the results of this study, there is compelling evidence to support that our lead vaccine formulation (CPS-CRM197 plus Hcp1) may be able to accomplish this goal. To our knowledge, this is the highest level of protection conferred by a subunit vaccine against an acute inhalational challenge of *B. pseudomallei*.

Collectively, these studies support use of multivalent subunit vaccines to immunize against disease caused by *B. pseudomallei*. Considering that high level protection was achieved against an acute inhalational challenge, such vaccines will be useful for both public health and biodefense purposes.

REFERENCES (EACH OF WHICH IS HEREBY INCORPORATED BY REFERENCE IN ITS ENTIRETY)

1. Limmathurotsakul D, Golding N, Dance D A, Messina J P, Pigott D M, Moyes C L, Rolim D B, Bertherat E, Day N P, Peacock S J, Hay S I. 2016. Predicted global distribution of *Burkholderia pseudomallei* and burden of melioidosis. Nat Microbiol 1:15008.
2. Currie B J, Kaestli M. 2016. Epidemiology: A global picture of melioidosis. Nature 529:290-1.
3. Dance D A B. 2000. Ecology of *Burkholderia pseudomallei* and the interactions between environmental *Burkholderia* spp. and human-animal hosts. Acta Tropica 74:159-168.
4. Wiersinga W J, van der Poll T, White N J, Day N P, Peacock S J. 2006. Melioidosis: insights into the pathogenicity of *Burkholderia pseudomallei*. Nat Rev Micro 4:272-282.
5. Chaowagul W, White N J, Dance D A B, Wattanagoon Y, Naigowit P, Davis T M E, Looareesuwan S, Pitakwatchara N. 1989. Melioidosis: A Major Cause of Community-Acquired Septicemia in Northeastern Thailand. Journal of Infectious Diseases 159:890-899.
6. Currie B J, Fisher D A, Howard D M, Burrow J N C, Lo D, Selva-nayagam S, Anstey N M, Huffam S E, Snelling P L, Marks P J, Stephens D P, Lum G D, Jacups S P, Krause V L. 2000. Endemic Melioidosis in Tropical Northern Australia: A 10-Year Prospective Study and Review of the Literature. Clinical Infectious Diseases 31:981-986.
7. Currie B J, Ward L, Cheng A C. 2010. The Epidemiology and Clinical Spectrum of Melioidosis: 540 Cases from the 20 Year Darwin Prospective Study. PLoS Negl Trop Dis 4: e900.
8. Suputtamongkol Y, Chaowagul W, Chetchotisakd P, Lertpatanasuwan N, Intaranongpai S, Ruchutrakool T, Budhsarawong D, Mootsikapun P, Wuthiekanun V, Teerawatasook N, Lulitanond A. 1999. Risk factors for melioidosis and bacteremic melioidosis. ClinInfectDis 29:408-413.
9. Chen Y L, Yen Y C, Yang C Y, Lee M S, Ho C K, Mena K D, Wang P Y, Chen P S. 2014. The concentrations of ambient *Burkholderia pseudomallei* during typhoon season in endemic area of melioidosis in Taiwan. PLoS Negl Trop Dis 8:e2877.
10. Cheng A C, Jacups S P, Gal D, Mayo M, Currie B J. 2006. Extreme weather events and environmental contamination are associated with case-clusters of melioidosis in the Northern Territory of Australia. Int J Epidemiol 35:323-9.

11. Currie B J, Jacups S P. 2003. Intensity of rainfall and severity of melioidosis, Australia. Emerg Infect Dis 9:1538-42.
12. Ko W C, Cheung B M, Tang H J, Shih H I, Lau Y J, Wang L R, Chuang Y C. 2007. Melioidosis outbreak after typhoon, southern Taiwan. Emerg Infect Dis 13:896-8.
13. Currie B J. 2015. Melioidosis: evolving concepts in epidemiology, pathogenesis, and treatment. Semin Respir Crit Care Med 36:111-25.
14. Rotz L D, Khan A S, Lillibridge S R, Ostroff S M, Hughes J M. 2002. Public health assessment of potential biological terrorism agents. Emerg Infect Dis 8:225-30.
15. Voskuhl G W, Cornea P, Bronze M S, Greenfield R A. 2003. Other bacterial diseases as a potential consequence of bioterrorism: Q fever, brucellosis, glanders, and melioidosis. J Okla State Med Assoc 96:214-7.
16. Titball R W, Burtnick M N, Bancroft G J, Brett P. 2017. *Burkholderia pseudomallei* and *Burkholderia mallei* vaccines: Are we close to clinical trials? Vaccine doi:10.1016/j.vaccine.2017.03.022.
17. Atkins T, Prior R, Mack K, Russell P, Nelson M, Prior J, Ellis J, Oyston P C, Dougan G, Titball R W. 2002. Characterisation of an acapsular mutant of *Burkholderia pseudomallei* identified by signature tagged mutagenesis. J Med Microbiol 51:539-47.
18. Nieves W, Asakrah S, Qazi O, Brown K A, Kurtz J, Aucoin D P, McLachlan J B, Roy C J, Morici L A. 2011. A naturally derived outer-membrane vesicle vaccine protects against lethal pulmonary *Burkholderia pseudomallei* infection. Vaccine 29:8381-9.
19. Nieves W, Petersen H, Judy B M, Blumentritt C A, Russell-Lodrigue K, Roy C J, Torres A G, Morici L A. 2014. A *Burkholderia pseudomallei* outer membrane vesicle vaccine provides protection against lethal sepsis. Clin Vaccine Immunol 21:747-54.
20. Silva E B, Goodyear A, Sutherland M D, Podnecky N L, Gonzalez-Juarrero M, Schweizer H P, Dow S W. 2013. Correlates of Immune Protection following Cutaneous Immunization with an Attenuated *Burkholderia pseudomallei* Vaccine. Infection and Immunity 81:4626-4634.
21. AuCoin D P, Reed D E, Marlenee N L, Bowen R A, Thorkildson P, Judy B M, Torres A G, Kozel T R. 2012. Polysaccharide Specific Monoclonal Antibodies Provide Passive Protection against Intranasal Challenge with *Burkholderia pseudomallei*. PLoS ONE 7:e35386.
22. Brett P J, Woods D E. 1996. Structural and immunological characterization of *Burkholderia pseudomallei* O-polysaccharide-flagellin protein conjugates. Infection and Immunity 64:2824-8.
23. Bryan L E, Wong S, Woods D E, Dance D A, Chaowagul W. 1994. Passive protection of diabetic rats with antisera specific for the polysaccharide portion of the lipopolysaccharide isolated from *Pseudomonas pseudomallei*. The Canadian journal of infectious diseases=Journal canadien des maladies infectieuses 5:170-8.
24. Chin C Y, Tan S C, Nathan S. 2012. Immunogenic recombinant *Burkholderia pseudomallei* MprA serine protease elicits protective immunity in mice. Front Cell Infect Microbiol 2:85.
25. Harland D N, Chu K, Haque A, Nelson M, Walker N J, Sarkar-Tyson M, Atkins T P, Moore B, Brown K A, Bancroft G, Titball R W, Atkins H S. 2007. Identification of a LolC Homologue in *Burkholderia pseudomallei*, a Novel Protective Antigen for Melioidosis. Infection and Immunity 75:4173-4180.
26. Scott A E, Burtnick M N, Stokes M G, Whelan A O, Williamson E D, Atkins T P, Prior J L, Brett P J. 2014. *Burkholderia pseudomallei* capsular polysaccharide conjugates provide protection against acute melioidosis. Infect Immun 82:3206-13.
27. Whitlock G C, Deeraksa A, Qazi O, Judy B M, Taylor K, Propst K L, Duffy A J, Johnson K, Kitto G B, Brown K A, Dow S W, Tones A G, Estes D M. 2010. Protective response to subunit vaccination against intranasal *Burkholderia mallei* and *B. pseudomallei* challenge. Procedia in Vaccinology 2:71-75.
28. Zhang S, Feng S H, Li B, Kim H Y, Rodriguez J, Tsai S, Lo S C. 2011. In vitro and In vivo studies on monoclonal antibodies with prominent bactericidal activity against *Burkholderia pseudomallei* and *Burkholderia mallei*. Clin Vaccine Immunol 2011:30.
29. Muruato L A, Tapia D, Hatcher C L, Kalita M, Brett P J, Gregory A E, Samuel J E, Titball R W, Torres A G. 2017. The Use of Reverse Vaccinology in the Design and Construction of Nano-glycoconjugate Vaccines against *Burkholderia pseudomallei*. Clin Vaccine Immunol doi: 10.1128/CVI.00206-17.
30. Burtnick M N, Heiss C, Roberts R A, Schweizer H P, Azadi P, Brett P J. 2012. Development of capsular polysaccharide-based glycoconjugates for immunization against melioidosis and glanders. Frontiers in Cellular and Infection Microbiology 2.
31. Perry M B, MacLean L L, Schollaardt T, Bryan L E, Ho M. 1995. Structural characterization of the lipopolysaccharide O antigens of *Burkholderia pseudomallei*. Infection and Immunity 63:3348-52.
32. Burtnick M N, Brett P J, Harding S V, Ngugi S A, Ribot W J, Chantratita N, Scorpio A, Milne T S, Dean R E, Fritz D L, Peacock S J, Prior J L, Atkins T P, Deshazer D. 2011. The cluster 1 type VI secretion system is a major virulence determinant in *Burkholderia pseudomallei*. Infect Immun 79:1512-25.
33. Pumpuang A, Dunachie S J, Phokrai P, Jenjaroen K, Sintiprungrat K, Boonsilp S, Brett P J, Burtnick M N, Chantratita N. 2017. Comparison of O-polysaccharide and hemolysin co-regulated protein as target antigens for serodiagnosis of melioidosis. PLoS Negl Trop Dis 11:e0005499.
34. Shanks J, Burtnick M N, Brett P J, Waag D M, Spurgers K, Ribot W J, Schell M A, Panchal R G, Gherardini F C, Wilkinson K D, DeShazer D. 2009. *Burkholderia mallei* tssM Encodes a Secreted Deubiquitinase That Is Expressed Inside Infected RAW 264.7 Cells. Infect Immun 77:1636-1648.
35. Lefeber D J, Benaissa-Trouw B, Vliegenthart J F, Kamerling J P, Jansen W T, Kraaijeveld K, Snippe H. 2003. Th1-directing adjuvants increase the immunogenicity of oligosaccharide-protein conjugate vaccines related to *Streptococcus pneumoniae* type 3. Infect Immun 71:6915-20.
36. Lin L, Gerth A J, Peng S L. 2004. CpG DNA redirects class-switching towards "Th1-like" Ig isotype production via TLR9 and MyD88. Eur J Immunol 34:1483-7.
37. Brady C, Killeen K, Taylor W, Patkar A, Lees A. 2012. new paradigm for rapidly translating novel conjugate vaccines into the clinic. BioProcess International 10:50-55.
38. Broker M, Costantino P, DeTora L, McIntosh E D, Rappuoli R. 2011. Biochemical and biological characteristics of cross-reacting material 197 CRM197, a non-toxic mutant of diphtheria toxin: use as a conjugation protein in vaccines and other potential clinical applications. Biologicals 39:195-204.

39. Plotkin S A. 2010. Correlates of protection induced by vaccination. Clin Vaccine Immunol 17:1055-65.
40. Reckseidler S L, DeShazer D, Sokol P A, Woods D E. 2001. Detection of Bacterial Virulence Genes by Subtractive Hybridization: Identification of Capsular Polysaccharide of *Burkholderia pseudomallei* as a Major Virulence Determinant. Infection and Immunity 69:34-44.
41. Pichichero M E. 2013. Protein carriers of conjugate vaccines: characteristics, development, and clinical trials. Hum Vaccin Immunother 9:2505-23.
42. Monteiro M A, Baqar S, Hall E R, Chen Y H, Porter C K, Bentzel D E, Applebee L, Guerry P. 2009. Capsule polysaccharide conjugate vaccine against diarrheal disease caused by *Campylobacter jejuni*. Infect Immun 77:1128-36.
43. Weintraub A. 2003. Immunology of bacterial polysaccharide antigens. Carbohydrate Research 338:2539-2547.
44. Lockhart S. 2003. Conjugate vaccines. Expert Review of Vaccines 2:633-648.
45. Snapper C M, Mond J J. 1996. A model for induction of T cell-independent humoral immunity in response to polysaccharide antigens. The Journal of Immunology 157:2229-33.
46. Scott A E, Ngugi S A, Laws T R, Corser D, Lonsdale C L, D'Elia R V, Titball R W, Williamson E D, Atkins T P, Prior J L. 2014. Protection against experimental melioidosis following immunisation with a lipopolysaccharide-protein conjugate. J Immunol Res 2014:392170.
47. Mulye M, Bechill M P, Grose W, Ferreira V P, Lafontaine E R, Wooten R M. 2014. Delineating the importance of serum opsonins and the bacterial capsule in affecting the uptake and killing of *Burkholderia pseudomallei* by murine neutrophils and macrophages. PLoS Negl Trop Dis 8:e2988.
48. Woodman M E, Worth R G, Wooten R M. 2012. Capsule influences the deposition of critical complement C3 levels required for the killing of *Burkholderia pseudomallei* via NADPH-oxidase induction by human neutrophils. PLoS ONE 7:e52276.
49. Burtnick M N, Brett P J. 2013. *Burkholderia mallei* and *Burkholderia pseudomallei* Cluster 1 Type VI Secretion System Gene Expression Is Negatively Regulated by Iron and Zinc. PLoS ONE 8:e76767.
50. Burtnick M N, Brett P J, DeShazer D. 2014. Proteomic analysis of the *Burkholderia pseudomallei* type II secretome reveals hydrolytic enzymes, novel proteins, and the deubiquitinase TssM. Infection and Immunity 82.
51. Tan K S, Chen Y, Lim Y C, Tan G Y, Liu Y, Lim Y T, Macary P, Gan Y H. 2010. Suppression of host innate immune response by *Burkholderia pseudomallei* through the virulence factor TssM. J Immunol 184:5160-71.
52. Dunachie S J, Jenjaroen K, Reynolds C J, Quigley K J, Sergeant R, Sumonwiriya M, Chaichana P, Chumseng S, Ariyaprasert P, Lassaux P, Gourlay L, Promwong C, Teparrukkul P, Limmathurotsakul D, Day N P J, Altmann D M, Boyton R J. 2017. Infection with *Burkholderia pseudomallei*—immune correlates of survival in acute melioidosis. Sci Rep 7:12143.
53. Jenjaroen K, Chumseng S, Sumonwiriya M, Ariyaprasert P, Chantratita N, Sunyakumthorn P, Hongsuwan M, Wuthiekanun V, Fletcher H A, Teparrukkul P, Limmathurotsakul D, Day N P, Dunachie S J. 2015. T-Cell Responses Are Associated with Survival in Acute Melioidosis Patients. PLoS Negl Trop Dis 9:e0004152.
54. Schully K L, Bell M G, Ward J M, Keane-Myers A M. 2014. Oropharyngeal aspiration of *Burkholderia mallei* and *Burkholderia pseudomallei* in BALB/c mice. PLoS One 9:e115066.
55. Titball R W. 2008. Vaccines against intracellular bacterial pathogens. Drug Discov Today 13:596-600.
56. Burtnick M N, Heiss C, Schuler A M, Azadi P, Brett P J. 2012. Development of novel O-polysaccharide based glycoconjugates for immunization against glanders. Frontiers in Cellular and Infection Microbiology 2.
57. Nuti D E, Crump R B, Dwi Handayani F, Chantratita N, Peacock S J, Bowen R, Felgner P L, Huw Davies D, Wu T, Lyons C R, Brett P J, Burtnick M N, Kozel T R, AuCoin D P. 2011. Identification of circulating bacterial antigens by in vivo microbial antigen discovery. MBio 2.
58. Burtnick M N, Heiss C, Schuler A M, Azadi P, Brett P J. 2012. Development of novel O-polysaccharide based glycoconjugates for immunization against glanders. Frontiers in Cellular and Infection Microbiology 2.
59. Massey S, Yeager L A, Blumentritt C A, Vijayakumar S, Sbrana E, Peterson J W, Brasel T, LeDuc J W, Endsley J J, Torres A G. 2014. Comparative *Burkholderia pseudomallei* natural history virulence studies using an aerosol murine model of infection. Sci Rep 4:4305.
60. Reed L J, Muench H. 1938. A simple method for estimating fifty percent end points. Am J Hyg 27:493-497.
61. Heiss C, Burtnick M N, Wang Z, Azadi P, Brett P J. 2012. Structural analysis of capsular polysaccharides expressed by *Burkholderia mallei* and *Burkholderia pseudomallei*. Carbohydr Res 349:90-4.
62. Holden M T G, Titball R W, Peacock S J, Cerdeño-Tárraga A M, Atkins T, Crossman L C, Pitt T, Churcher C, Mungall K, Bentley S D, Sebaihia M, Thomson N R, Bason N, Beacham I R, Brooks K, Brown K A, Brown N F, Challis G L, Cherevach I, Chillingworth T, Cronin A, Crossett B, Davis P, DeShazer D, Feltwell T, Fraser A, Hance Z, Hauser H, Holroyd S, Jagels K, Keith K E, Maddison M, Moule S, Price C, Quail M A, Rabbinowitsch E, Rutherford K, Sanders M, Simmonds M, Songsivilai S, Stevens K, Tumapa S, Vesaratchavest M, Whitehead S, Yeats C, Barrell B G, Oyston P C F, Parkhill J. 2004. Genomic plasticity of the causative agent of melioidosis, *Burkholderia pseudomallei*. Proceedings of the National Academy of Sciences of the United States of America 101:14240-14245.

Example 2

This example demonstrates synthesis of Bt CPS-CRM197 using CPS purified from *Burkholderia thailandensis* BT2683 which can be used to immunize against disease caused by *B. pseudomallei*, *B. thailandensis* or *B. mallei*.

Bacterial strains and growth conditions. *Burkholderia thailandensis* BT2683 was cultured in LB broth or on LB agar. Bacterial cultures were incubated at 37° C.; broth cultures were incubated with shaking (200 rpm). Bacterial stocks were maintained at −80° C. as 20% glycerol suspensions.

CPS purification. Broth in 2 L baffled Erlenmeyer flasks was inoculated with *Burkholderia thailandensis* BT2683 and incubated overnight at 37° C. with shaking (200 rpm). Cell pellets were obtained by centrifugation and extracted using a modified hot aqueous-phenol procedure (31). Purified CPS antigens were then obtained essentially as previously described (58).

Bt CPS-CRM197 glycoconjugate synthesis. Recombinant, pre-clinical grade CRM197 was purchased from Reagent Proteins. The CPS-CRM197 glycoconjugates used in this study were synthesized. Briefly, purified CPS was solubilized at 5 mg/ml in PBS (BupH; Pierce) and added to a small amber vial. To each ml of the CPS solution was added ~6 mg (~30 mM) of sodium meta-periodate. Once the crystals had dissolved, the reaction mixture was incubated for ~40 minutes at room temperature with stirring. To remove any excess oxidizing agent, the reaction mixture was applied to a Zeba Desalt Spin Column (Pierce) equilibrated with either PBS or BB (Pierce) and the eluate was collected. To facilitate conjugation of the CPS to the carrier protein (CRM197 buffer exchanged at 5 mg/ml into either PBS or BB on a Zeba column), the activated CPS was added to small amber vial. To each ml of the CPS solution was added 500 µl of the carrier protein (5 mg/ml stock). Following mixing by gentle agitation, 10 µl of a 1 M sodium cyanoborohydride stock (in 10 mM NaOH) was added to each milliliter of the conjugation mixture and the reaction incubated at 37° C. for 10 days with stirring. The conjugate reaction was then dialyzed against dH$_2$O using a 3500 MWCO Slide-A-Lyzer cassette (Pierce), syringe filter (0.45 µM) sterilized and lyophilized. BCA assay (Pierce) was used to quantitate the protein concentration of the glycoconjugate stock (the remainder of the mass was assumed to be polysaccharide).

Figure 11:
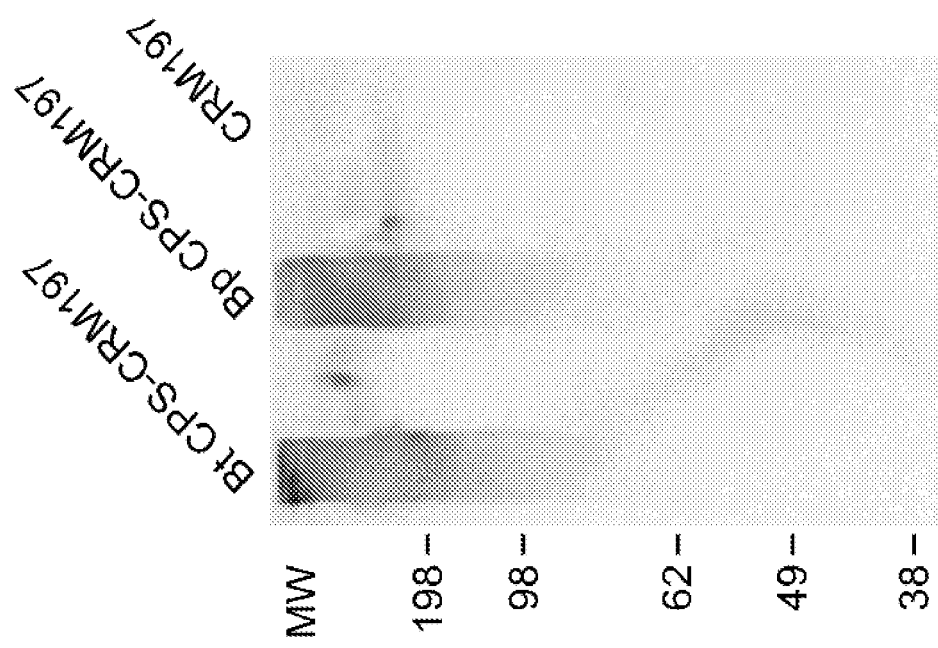

SDS-PAGE and Western immunoblotting. Glycoconjugate samples were solubilized in 1×SDS-PAGE sample buffer and heated to 100° C. for 5 minutes prior to electrophoresis on 4-12% a Bis-Tris gel (Invitrogen). Protein was visualized via staining with SimplyBlue Safe Stain (see FIG. 10). For Western immunoblot analyses, the glycoconjugate samples and controls were separated on the same 4-12% gels and electrophoretically transferred to nitrocellulose membranes. The membranes were blocked with StartingBlock for 30 minutes at room temperature and then incubated for 1 hour at room temperature with a 1/2000 dilution of a *Burkholderia pseudomallei* CPS-specific mAb (4C4). To facilitate detection, the membranes were incubated for 1 hour at room temperature with 1/5000 dilutions of an anti-mouse IgG horse radish peroxidase conjugate (SouthernBiotech). Blots were visualized using Pierce ECL Western Blotting Substrate (Thermo Scientific) and a ChemiDoc XRS imaging system (BioRad) (see FIG. 11).

TABLE 2

| Bacterial strains. | |
|---|---|
| Strains | Description$^a$ |
| *Burkholderia thailandensis* (Bt) | |
| E555 | Wild type: expresses a 6-deoxyheptan capsule that is identical to that expressed by *Burkholderia pseudomallei* (Bp) and *Burkholderia mallei* (Bm) |

TABLE 2-continued

| Bacterial strains. | |
|---|---|
| Strains | Description$^a$ |
| BT2683 | OPS-deficient derivative of E555: ΔrmlD |

Collectively, these studies support use of multivalent subunit vaccines generated from *B. thailandensis* to immunize against disease caused by *B. pseudomallei*, *B. thailandensis* or *B. mallei*.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition comprising a conjugate molecule, a *Burkholderia* hemolysin co-regulated protein (Hcp1), and a physiologically acceptable carrier, wherein the conjugate molecule comprises 6-deoxyheptan capsular polysaccharide (CPS) from *Burkholderia pseudomallei*, *Burkholderia thailandensis* or *Burkholderia mallei* covalently linked to recombinant CRM197 diphtheria toxin mutant (CRM197), and wherein the Hcp1 is purified recombinant *B. pseudomallei* Hcp1 or purified recombinant *B. mallei* Hcp1.

2. The composition of claim 1, wherein the CPS is covalently linked to the CRM197 via an amine linkage.

3. The composition of claim 1, wherein the Hcp1 is purified recombinant *B. pseudomallei* Hcp1.

4. A vaccine composition comprising an immunologically effective amount of the composition of claim 1.

5. A vaccine composition comprising an immunologically effective amount of the composition of claim 3.

6. The composition of claim 1, wherein the Hcp1 is purified recombinant *B. mallei* Hcp1.

7. A vaccine composition comprising an immunologically effective amount of the composition of claim 6.

8. A method of eliciting a protective immune response in a subject, the method comprising administering to the subject (i) an effective amount of a conjugate molecule comprising 6-deoxyheptan capsular polysaccharide (CPS) from *Burkholderia pseudomallei*, *Burkholderia thailandensis* or *Burkholderia mallet* covalently linked to recombinant CRM197 diphtheria toxin mutant (CRM197), and (ii) an effective amount of a *Burkholderia* hemolysin co-regulated protein (Hcp1), wherein the Hcp1 is recombinant *B. pseudomallei* Hcp1 or recombinant *B. mallei* Hcp1.

9. The method of claim 8, wherein the Hcp1 is recombinant *B. pseudomallei* Hcp1.

10. The method of claim 8, wherein the Hcp1 is recombinant *B. mallei* Hcp1.

11. The method of claim 8, wherein the CPS is covalently linked to the CRM197 via an amine linkage.

* * * * *

UNITED STATES PATENT AND TRADEMARK OFFICE
CERTIFICATE OF CORRECTION

| | |
|---|---|
| PATENT NO. | : 11,235,046 B2 |
| APPLICATION NO. | : 16/760418 |
| DATED | : February 1, 2022 |
| INVENTOR(S) | : Brett et al. |

It is certified that error appears in the above-identified patent and that said Letters Patent is hereby corrected as shown below:

In the Claims

Claim 8
Column 30, Line 48:
"mallet"
Should read:
--mallei--

Signed and Sealed this
Third Day of May, 2022

Katherine Kelly Vidal
*Director of the United States Patent and Trademark Office*